(12) United States Patent
Day

(10) Patent No.: US 9,034,264 B2
(45) Date of Patent: May 19, 2015

(54) BIOSENSOR

(71) Applicant: Highland Biosciences Limited

(72) Inventor: Richard Day, Inverness Highland (GB)

(73) Assignee: Highland Biosciences Limited, Inverness Highland (GB)

( * ) Notice: Subject to any disclaimer, the term of this patent is extended or adjusted under 35 U.S.C. 154(b) by 0 days.

(21) Appl. No.: 14/466,446

(22) Filed: Aug. 22, 2014

(65) Prior Publication Data

US 2015/0000397 A1 Jan. 1, 2015

Related U.S. Application Data

(63) Continuation of application No. 12/518,612, filed as application No. PCT/GB2007/050791 on Dec. 27, 2007, now Pat. No. 8,845,968.

(30) Foreign Application Priority Data

Dec. 28, 2006 (GB) .................................. 0626004.6
Oct. 24, 2007 (GB) .................................. 0720874.7

(51) Int. Cl.
*G01N 27/00* (2006.01)
*G01N 29/036* (2006.01)
(Continued)

(52) U.S. Cl.
CPC .............. *G01N 29/036* (2013.01); *G01N 9/002* (2013.01); *G01N 11/16* (2013.01); *G01N 29/022* (2013.01);
(Continued)

(58) Field of Classification Search
CPC .... G01L 1/162; G01L 9/0022; G01N 29/022; G01N 2291/02818; G01N 9/002; G01N 2009/006; G01N 2291/014

USPC .............. 73/64.41–64.42; 422/430, 68.1, 73, 422/82.01; 436/66, 69–70; 435/13, 283.1, 435/287.1
See application file for complete search history.

(56) References Cited

U.S. PATENT DOCUMENTS 4,469,979 A 9/1984 Chuang
4,594,898 A 6/1986 Kirman et al.
(Continued)

FOREIGN PATENT DOCUMENTS

EP 0112156 6/1984
EP 0282251 9/1988
(Continued)

OTHER PUBLICATIONS

Zhang et al.; "Determination of liquid density with a low frequency mechanical sensor based on quartz tuning fork"; Sensors and Actuators B 84 (2002) 123-128.
(Continued)

*Primary Examiner* — Dennis M White
(74) *Attorney, Agent, or Firm* — Moore & Van Allen PLLC; W. Kevin Ransom

(57) ABSTRACT

The present application provides apparatus and methods for determining the density of a fluid sample. In particular, it provides a sensor device which can be loaded with a fluid sample such as blood, and which further comprises at least one oscillating beam member or resonator. Exposure of the blood sample to clotting agents allows a clotting reaction to commence. The device allows the density of the sample fluid to be monitored with reference to the oscillation of the vibrating beam member, thus allowing the monitoring of the clotting of the fluid sample.

16 Claims, 18 Drawing Sheets

(51) Int. Cl.

| | | |
|---|---|---|
| G01N 9/00 | (2006.01) | |
| G01N 11/16 | (2006.01) | |
| G01N 29/02 | (2006.01) | |
| G01N 29/22 | (2006.01) | |
| G01N 29/24 | (2006.01) | |
| G01N 29/44 | (2006.01) | |
| G01N 33/49 | (2006.01) | |

(52) U.S. Cl.
 CPC ............ *G01N 29/222* (2013.01); *G01N 29/245* (2013.01); *G01N 29/4427* (2013.01); *G01N 33/4905* (2013.01); *G01N 2291/0255* (2013.01); *G01N 2291/02818* (2013.01); *G01N 2291/0427* (2013.01); *G01N 33/49* (2013.01); *G01N 2291/014* (2013.01); *G01N 2291/022* (2013.01); *G01N 2291/101* (2013.01)

(56) References Cited

U.S. PATENT DOCUMENTS

| | | | |
|---|---|---|---|
| 4,602,505 | A | 7/1986 | Kanda et al. |
| 4,679,427 | A | 7/1987 | Kanda et al. |
| 4,878,386 | A | 11/1989 | Isobe |
| 4,920,787 | A | 5/1990 | Dual et al. |
| 4,922,745 | A | 5/1990 | Rudkin et al. |
| 4,947,694 | A | 8/1990 | Kirman et al. |
| 5,020,370 | A | 6/1991 | Deval et al. |
| 5,095,763 | A | 3/1992 | Delatorre |
| 5,211,054 | A | 5/1993 | Muramatsu et al. |
| 5,494,639 | A | 2/1996 | Grzegorzewski |
| 5,892,144 | A | 4/1999 | Meller et al. |
| 5,962,786 | A | 10/1999 | Traon et al. |
| 5,987,987 | A | 11/1999 | Watarai |
| 6,044,694 | A | 4/2000 | Anderson et al. |
| 6,046,051 | A | 4/2000 | Jina |
| 6,200,532 | B1 | 3/2001 | Wu et al. |
| 6,311,549 | B1 | 11/2001 | Thundat et al. |
| 6,336,353 | B2 | 1/2002 | Matsiev et al. |
| 6,360,600 | B1 | 3/2002 | Kuroki |
| 6,401,519 | B1 | 6/2002 | McFarland et al. |
| 6,412,354 | B1 | 7/2002 | Birchak et al. |
| 6,746,872 | B2 | 6/2004 | Zheng et al. |
| 6,904,786 | B2 | 6/2005 | Matsiev et al. |
| 6,907,785 | B1 | 6/2005 | Gallagher |
| 7,043,969 | B2 | 5/2006 | Matsiev et al. |
| 7,073,370 | B2 | 7/2006 | Matsiev et al. |
| 7,178,378 | B2 | 2/2007 | Crawley et al. |
| 7,334,452 | B2 | 2/2008 | Matsiev et al. |
| 7,562,557 | B2 | 7/2009 | Bennett et al. |
| 7,674,616 | B2 | 3/2010 | Farnam et al. |
| 2002/0174730 | A1 | 11/2002 | Drahm et al. |
| 2002/0187071 | A1 | 12/2002 | Law |
| 2004/0099050 | A1 | 5/2004 | Matsiev et al. |
| 2004/0244487 | A1 | 12/2004 | Kolosov et al. |
| 2005/0209796 | A1 | 9/2005 | Kolosov et al. |
| 2005/0244299 | A1 | 11/2005 | Dasgupta et al. |
| 2006/0010964 | A1 | 1/2006 | Sparks et al. |
| 2006/0035298 | A1 | 2/2006 | Hill et al. |
| 2006/0110283 | A1 | 5/2006 | Fish |
| 2006/0170311 | A1 | 8/2006 | Jones et al. |
| 2006/0213552 | A1 | 9/2006 | Sparks et al. |
| 2006/0218996 | A1 | 10/2006 | Matsiev et al. |
| 2006/0281140 | A1 | 12/2006 | Ranby |
| 2007/0017291 | A1 | 1/2007 | Cypes et al. |
| 2007/0077610 | A1 | 4/2007 | Ghai et al. |
| 2007/0144240 | A1 | 6/2007 | Andle |
| 2008/0110247 | A1 | 5/2008 | Shaw et al. |

FOREIGN PATENT DOCUMENTS

| | | |
|---|---|---|
| EP | 0304283 | 2/1989 |
| EP | 0737853 | 10/1996 |
| EP | 0737853 A1 | 10/1996 |
| EP | 1329723 | 7/2003 |
| EP | 1443325 | 8/2004 |
| EP | 1519162 | 3/2005 |
| EP | 1674865 | 6/2006 |
| EP | 1674865 A1 | 6/2006 |
| EP | 1804048 | 7/2007 |
| EP | 1901065 | 3/2008 |
| GB | 2075762 | 11/1981 |
| GB | 2280751 | 2/1995 |
| GB | 2303450 | 2/1997 |
| GB | 2445163 | 7/2008 |
| JP | 11-094726 | 4/1999 |
| JP | 11094726 | 4/1999 |
| SU | 682796 | 8/1979 |
| SU | 744277 | 6/1980 |
| SU | 759908 | 8/1980 |
| SU | 898288 | 1/1982 |
| WO | WO94/14047 | 6/1994 |
| WO | WO98/09139 | 3/1998 |
| WO | WO99/18431 | 4/1999 |
| WO | WO00/04370 | 1/2000 |
| WO | WO00/31529 | 6/2000 |
| WO | WO 2004/036191 | 4/2004 |
| WO | WO2004/036207 | 4/2004 |
| WO | WO 2004/068138 | 8/2004 |
| WO | WO2004/070335 | 8/2004 |
| WO | WO2004/086002 | 10/2004 |
| WO | WO 2004/086003 | 10/2004 |
| WO | WO 2004/086027 | 10/2004 |
| WO | WO2004/094987 | 11/2004 |
| WO | WO 2005/043126 | 5/2005 |
| WO | WO 2005/103645 | 11/2005 |
| WO | WO2005/103674 | 11/2005 |
| WO | WO2005/114138 | 12/2005 |
| WO | WO2006/031072 | 3/2006 |
| WO | WO2006/067504 | 6/2006 |
| WO | WO2006/094694 | 9/2006 |
| WO | WO2007/034152 | 3/2007 |
| WO | WO2007/077038 | 7/2007 |
| WO | WO 2007/101993 | 9/2007 |
| WO | WO/2009/014830 | 1/2009 |

OTHER PUBLICATIONS

Cheshmehdoost et al.; "Characteristics of a force transducer incorporating a mechanical DETF resonator"; Sensors and Actuators A vol. 26, No. 1-3, Mar. 1, 1991, pp. 307-312.

Langdon et al.; "Resonator sensors—a review;" Journal of Physics E Scientific Instruments. vol. 18, No. 2, Feb. 1, 1985, pp. 103-115.

Dring et al.; "Integrated on-line multisensing of fluid flow using a mechanical resonator"; Sensors and Actuators vol. 85, No. 1-3, Aug. 25, 2000, pp. 275-279.

Ward et al.; IEEE Transactions on Ultrasonics, Ferroelectrics and Frequency Control, vol. 35, No. 3, May 1988; pp. 323-330.

Green et al.; "Liquid Density Measurements using a Double-Ended Tuning Fork Resonator"; Proceedings of International IMEKO Conference ISMQC 95/CIMI 95, Zaragoza, Oct. 1995, pp. 401-410.

Green et al.; "Measurement of Liquid Density Using a Double-Ended Tuning Fork Resonator, Measurement and Control"; vol. 29, Sep. 1996, pp. 208-210.

Nicu et al.; "Modeling of a tuning fork biosensor based on the excitation of one particular resonance mode"; IOP Publishing J. Micromech. Microeng. 14 (2004) 727-736.

Cotton et al.; "A new binderless thick-film piezoelectric paste"; J Mater Sci.: Mater Electron (2007) 18:1037-1044.

S.P. Beeby et al., "Thick-film PZT-silicon micromechanical resonator", Electronic Letters, Sep. 14, 2000, vol. 36, No. 19.

T. Yan et al., "Thick-film PZT-metallic triple beam resonator", Electronic Letters, Jun. 26, 2003, vol. 39, No. 13, pp. 982-983.

Michael Rodahl et al., "Quartz crystal microbalance setup for frequency and Q-factor measurements in gaseous and liquid environments", Review of Scientific Instruments, vol. 66, No. 7, Jul. 1995, pp. 3924-3930.

"A & D's Tuning-fork Vibro Viscometer, Is Now a National Standard in Japan" Flyer, A&D Company Limited.

Richard Dewar et al., "The quartz crystal microbalance as a microviscometer for improved rehabilitation therapy of dysphagic

(56) References Cited

OTHER PUBLICATIONS patients", Proceedings of the 2005 IEEE, Engineering in Medicine and Biology 27th Annual Conference, Shanghai, China, Sep. 1-4, 2005, pp. 2511-2515.

D. S. Randall et al., "A pressure transducer using a metallic triple-beam tuning fork", Sensors and Actuators A vol. 60 (1997), pp. 160-162.

Christopher R. Kirkendall et al., "Liquid Damping Isolation on Quartz Crystal Microbalance for Effective Preservation of High Quality Factor and Sensitivity in Liquid", IEEE Sensors 2009 Conference, pp. 607-610.

Ana Maria Cao-Paz et al., "Resolution in QCM Sensors for the Viscosity and Density of Liquids: Application to Lead Acid Batteries", Sensors 2012, vol. 12, pp. 10604-10620.

Green, "Thesis"; Brunel University, 1995.

E. Benes et al., "Sensors based on piezoelectric resonators"; Sensors and Actuators A, vol. 48, No. 1, May 1, 1995, pp. 1-21.

Reichel et al, "Measurement of Liquid Properties Using a Vibrating Micromachined Clamped-Clamped Beam Structure"; SENSOR Conference 2007 Proceedings II, pp. 33-38.

Eernise et al.; "Survey of Quartz Bulk Resonator Sensor Technologies"; IEEE TRANS on Ultrasonics, Ferroelectrics and Frequency Control, vol. 35, No. 3, May 1988, p. 323.

Torah et al.; "A Study of powder size combinations for improving piezo electric properties of PZT thick-film devices The 17th European Conference on Solid State Transducers (Eurosensors XVII)", Sep. 21-24, 2003, Portugal. pp. 610-613.

Lavrik et al: "Cantilever transducers as a platform for chemical and biological sensors"; Review of Scientific Instruments, vol. 75, No. 7, pp. 2229-2253, Jul. 2004.

Beeby: "Mechanical Transduction Techniques"; MEMS Mechanical Sensors, Chapter 5, pp. 85-112, 2004.

Su et al: "Quartz tuning fork biosensor"; Biosensors & Bioelectronics, vol. 17, pp. 111-117, 2002.

Riesch et al: "A Novel Sensor System for Liquid Properties Based on a Micromachined Beam and a Low-Cost Optical Readout"; IEEE Sensors 2007 Conference, pp. 872-875.

Etchart et al: "MEMS sensors for density-viscosity sensing in a low-flow microfluidic environment"; Sensors and Actuators, vol. A 141, pp. 266-275, 2008.

Dring et al: "Integrated on-line multisensing of fluid flow using a mechanical"; Sensors and Actuators, vol. 85, pp. 275-279, 2000.

Shih et al: "Simultaneous liquid viscosity and density determination with piezoelectric unimorph cantilevers"; Journal of Applied Physics, vol. 89, No. 2, pp. 1497-1505, Jan. 15, 2001.

Tamayo et al: "Chemical sensors and biosensors in liquid environment based on microcantilevers with amplified quality factor"; Ultramicroscopy, vol. 86, pp. 167-173, 2001.

Tamayo et al: "Digital tuning of the quality factor of micromechanical resonant biological detectors"; Sensors and Actuators, vol. B 89, pp. 33-39, 2003.

Yan et al: "Metallic Triple Beam Resonator with Thick-film Printed Drive and Pickup"; Eurosensors XVII, 2003.

Seo et al: "Novel High Q-Factor Resonant Microsensor Platform for Chemical and Biological Applications"; Solid State Sensors Actuators and MicroSystems, vol. 1, pp. 593-596, 2005.

Gfeller et al: "Rapid Biosensor for Detection of Antibiotic-Selective Growth of *Escherichia coli*"; Applied and Environmental Microbiology, vol. 71, No. 5, pp. 2626-2631, May 2005.

Burg et al: "Vacuum-Packaged Suspended Microchannel Resonant Mass Sensor for Biomolecular Detection"; Journal of Microelectromechanical Systems, vol. 15, No. 6, pp. 1466-1476, Dec. 2006.

Zhang J et al: "Determination of liquid density with a low frequency mechanical sensor based on quartz tuning fork"; Sensors and Actuators B, Elsevier Sequoia S.A., Lausanne, CH, vol. 84, No. 2-3, May 15, 2002, pp. 123-128, XP004360379.

International Search Report for PCT/GB2007/050791, dated Apr. 29, 2008.

BIOSENSOR

CLAIM OF PRIORITY UNDER 35 U.S.C. §119

The present Application for Patent claims priority to Non-Provisional application Ser. No. 12/518,612 entitled "Biosensor" filed Jun. 10, 2009 which claims priority to PCT Application No. PCT/GB2007/050791 entitled "Biosensor" filed Dec. 27, 2007 which claims priority to GB0626004.6 filed on Dec. 28, 2006 entitled "Disposable Test Strips and Associated Method for Measuring Viscosity and Density Changes in a Biological Fluid" and GB 0720874.7 filed on Oct. 24, 2007 entitled "Biosensor." All assigned to the assignee hereof and hereby expressly incorporated by reference herein.

FIELD OF THE INVENTION

The present invention relates to a device for measuring the viscosity and density of a fluid. More specifically, the present invention provides a disposable device for the measurement of the viscosity and/or density of a biological fluid sample. The present invention further extends to methods for the measurement of the viscosity and/or density of a liquid sample, and further to the use of the device of the present invention in such methods.

BACKGROUND OF THE INVENTION

When the body is injured, damage to the vascular vessels results in the loss of blood from the vasculature. To prevent continued blood loss, the body stops this flow of blood by means of haemostasis, which causes the formation of a blood clot or thrombosis.

Whilst blood clotting is essential for the repair of wounds, thrombosis can occur anywhere within the circulatory system. As such, thrombosis is a major cause of death due to restricted blood flow to vital organs. A thrombosis which forms within the blood vessels of the heart, lungs, brain or limbs can be particularly life threatening, causing conditions such as heart attack, stroke and deep vein thrombosis. Individuals who have undergone surgery, suffer from heart disease or who are at risk of thrombosis, are prescribed drugs such as the anti-coagulant Warfarin, to prevent unwanted thrombosis formation within blood vessels. Such medications are highly potent with long-lasting effects. For example, the drug Warfarin has a half-life in the body of around 2.5 days. Overlap between maintenance doses and the effects of lifestyle and other medications mean that efficient monitoring is critical to enable management of the dosage of anti-coagulant drugs. The administration of too much anti-coagulant medication can cause haemorrhaging, whilst too little can result in the formation of unwanted clotting.

There are a number of clinical tests that are used to routinely determine the level of anti-coagulant agents present in a blood sample. Of these, one of the most common is the prothrombin time (PT) test. The PT test measures the time taken for a sample of blood to clot in the presence of a clotting agent such as Thromboplastin and calcium. The amount of anticoagulant present in a sample can be determined as it is inversely proportional to the clotting time. Differences in the type of Thromboplastin administered leads to variations in results between different equipment manufacturers and laboratories when performing the PT test. To overcome this, the medical field has adopted the Internationalised Normalised Ratio (INR) to express PT.

Another test used to determine the level of anti-coagulant agents present in a blood sample is the Activated Partial Thromboplastin Test (APTT). In this test, a sample of plasma is tested by adding phospholipids, an activator (for example, ellagic acid, kaolin or micronised silica) and calcium. Formation of Xase and prothrombinase complexes on the surface of the phospholipids enables prothrombin to be converted to thrombin, with subsequent clot formation. The result of this test is determined with reference to the time for clot formation. The APTT test is used to evaluate the intrinsic coagulation pathway, which includes factors I, II, V, VIII, IX, X, XI and XII, and is generally performed in a clinical laboratory.

A further test is the ACT (activated clotting time) test, which resembles the APTT test, but uses a sample of whole blood. Other useful tests have been developed, including immunochemical assays for activation peptide factor IXa, anti-thrombin, Protein C and Protein S.

In recognizing the need for the provision of further tests which can be used to quickly and reliably determine levels of anti-coagulants in a blood sample, the present inventor, following extensive experimentation, has provided a device which has utility in the measurement of the viscosity and/or density of a fluid sample. The device can be used to determine blood clotting, and as such can be used to provide a quick and accurate determination of the levels of clotting factors, such as anti-coagulants in a blood sample.

SUMMARY OF THE INVENTION

According to a first aspect of the present invention there is provided a sensor device for determining and/or monitoring changes in the density and/or viscosity of a fluid, before, during and after a biochemical reaction, the device comprising;

a plurality of layers, wherein one of said layers comprises a base substrate, at least 2 beam members being defined by said base substrate, at least one vibration excitory element for use in providing the selective oscillation of at least one of said beam members, a sensor element for use in determining the frequency of oscillation of at least one of said beam members, and a reaction chamber, said reaction chamber defining an internal volume which is suitable for receiving and retaining a fluid sample, and wherein said reaction chamber accommodates said at least 2 beam members in a manner which allows the unimpeded oscillation of said at least 2 beam members.

In certain embodiments the at least 2 beam members are defined by, or are integral to the base substrate. That is, that the at least 2 beam members are formed of the material which comprises the base substrate. In alternative embodiment, the at least 2 beam members are formed independently of the base substrate, with said beam members being conjoined to said base substrate at either ends of their length. As herein defined, the area wherein the end of a beam members is conjoined to the base substrate is known as the decoupling zone.

In certain embodiments, the device comprises 2 beam members. In certain further embodiments, the device comprises 3 beam members. Certain further embodiments may provide devices comprising 4 or more beam members. Typically the beam members are spaced evenly apart in distance. Typically, the beam members are arranged such that they are generally parallel to each other. As such, in certain embodiments, said beam members are provided in a longitudinal direction, with said further beam members being provided in general register with the beam and positioned in a parallel orientation, said parallel beam members being spaced equidistantly from the other beam member.

In certain embodiments, the length of the beam members is around 18 mm in a lengthwise direction, the length being determined by the side of the beam which is of the greatest distance in length. The dimension of the beam which is perpendicular to the length is defined as the width, the width being of a distance which is smaller than the length.

In certain embodiments, where a triple beam (3 beam) arrangement is provided, the width of the centre beam may be around 2.0 mm, while the width of the outer beams, that is the beams which are placed either side of the central beam in a equidistant, parallel arrangement, may be around 1.0 mm. In certain embodiments, the width of the centrally positioned beam is the sum of the width of the two outer beams. The 3-beam embodiment of the present invention may exhibit 3 modes of vibration as follows: (i) all 3 tines oscillate in a unitary phase, (ii) the central tine does not oscillate, while the outer tines oscillate at a phase of 180 degrees with respect to each other, (iii) the central tine vibrates in anti-phase with respect to the oscillation of the outer tines, this being the optimum operation mode as bending moments and shearing forces at the decoupling zone located where the beam members are conjoined to the main body of the base substrate layer of the sensor.

In certain embodiments, the beam members have a thickness T and a width w, where the overall dimensions may be defined with reference to the formula $T/w \geq 0.1$.

In certain embodiments, each resonating beam member is capable of being resonated at a frequency of between about 1 kHz to about 500 kHz.

Typically, the beam members are composed of a material which allows them to resonate or oscillate. In certain embodiments, the material from which the beam structures are substantially composed is an inert material.

In certain embodiments where the beam members are not defined from, or integral to the material of the base substrate, the beam members are composed of a material which is selected from the group comprising, but not limited to: silicon, gold, platinum and steel. In embodiments where the beam members are comprised of steel, typically this is stainless steel.

In embodiments where the beam members are an integral part of the base substrate, said beam members may be formed by a technique selected from, but not limited to: etching, in particular photochemical etching, laser treatment and mechanical punching of the base substrate.

In certain embodiments, the vibratory element which mediates oscillation of one of the beam members is a piezoelectric element. The piezoelectric element, which may also be referred to as a piezoelectric actuator, may be conjoined to the beam member to be actuated at any suitable position which results in the actuation of the beam member. In certain embodiments, the piezoelectric material is electrically connected. Typically the piezoelectric element serves to cause oscillation of the beam element to which it is conjoined at the fundamental frequency. Alternatively the piezoelectric material can mediate oscillation of the beam member at a harmonic frequency.

The piezo electric material may be any suitable piezo electric material known to the person of general skill in the field, and may in particular be selected from the group comprising a polymer such as PVDF (polyvinylidenedifluoride), a crystal or a ceramic material. In certain further embodiments, the piezoelectric material is PZT. In certain embodiments, the PZT is provided in the form of a screen printed PZT actuator. Optionally, the screen printing is thick film printing of the PZT.

The application of electrical power to the piezoelectric material results in the vibration of the piezoelectric material and in turn the vibration of the conjoined beam member, or of at least one beam member which is located near to the piezoelectric material in cases where the piezoelectric actuator is provided upon the base substrate as opposed to the actual resonant beam. This vibration may alternatively be referred to as actuation of the beam member.

In certain further embodiments, the vibrational movement of the beam member is induced by magnetostriction or by direct magnetic actuation mediated by magnetic shape memory materials. Accordingly, in certain further embodiments, the vibration excitory element may be magnetic shape memory materials. Such materials include, but are not limited to ferromagnetic shape memory (FSM) alloys which exhibit large changes in shape and size upon application of a magnetic field.

In certain further embodiments, vibratory oscillation of a beam member may be achieved by a vibratory element which is provided in the form of a transducer which converts electrical energy into kinetic energy in the form of a resonance vibration at a specific frequency. The transducer may be connected to any suitable electrical energy source. A connecting means conjoins the transducer to the beam member allowing the kinetic energy to be transmitted from the transducer to the beam member, this resulting in vibration of the beam member.

In certain embodiments, electrical conductors, contacts and/or connections connect the vibratory element to an external control unit. These electrical connectors function to supply electrical power to the vibratory element. In certain embodiments, an insulating layer may be provided which covers the electrical contacts to prevent short circuiting.

In certain embodiments, the vibratory element causes at least one of the beam members to resonate in a transverse direction. The phase of the resonation is a function of the vibration mode. The vibration mode can be selected by exciting the vibration excitory element (resonator) within a predefined frequency range. Different resonant modes are achieved by selecting different energy states. Typically, the strongest energy state is selected, said state being out of phase by exciting the resonant beam at a particular frequency.

In certain embodiments, oscillation of the beam members can be detected by a sensor element. This sensor element determines the frequency of oscillation of at least one of the resonating beam members.

In certain embodiments, where a vibration excitory element is conjoined to at least one beam member, the sensor element is conjoined to a different beam member. In embodiments where the vibration excitory element is conjoined to the base substrate, as opposed to a specific beam member, the sensor element may be conjoined to a beam member, or alternatively, may be applied to the base substrate, in the proximity of the beam members. In further embodiments, a plurality of sensor means may be used. Said plurality of sensor means may be conjoined to, or associated with different beam members, to the base substrate or to both the resonating beam members and further to the base substrate in a manner and in a position which is suitable to allow the determination of the oscillation of at least one beam member. In embodiments where the sensor means is conjoined directly to the base substrate, typically said sensor is applied to an area which is proximal to the end of the length of the beam member. Typically, the sensor means is conjoined to the beam member in a position which is proximal to the end of the beam members, but at an end opposite to that where the vibration excitory element is provided. This spatial separation of the vibratory element and the sensor element (which may also be achieved by conjoining the vibratory element and the sensor element to different beam members) ensures that the sensor detects only oscillation of the beam member, and is not influenced directly by the vibration which is being emitted from the vibratory element.

In certain embodiments, the sensor means is a piezoelectric member, or substantially comprised of a piezoelectric material. This piezoelectric member, which may also be referred to as a piezoelectric element, detects the physical movement of the beam member during oscillation and turns this into a measurable signal. The sensor means may further have electrical connectors conjoined thereto, in order that an output signal can be output to a device or processing unit which can use the output signal as a measurable signal in order that the oscillation of at least one of the beam members with which the piezoelectric member is conjoined, associated with or proximal to can be determined.

Typically, the sensor means for determining the frequency of oscillation of at least one of the beam members is conjoined directly to that beam member. Generally, the beam member with which the piezoelectric member is conjoined is not also directly conjoined to a vibratory element. In embodiments where there are 3 or more beam members, sensor means for determining the frequency of oscillation of the beam members may be conjoined to more than one of said beam members, said beam members typically being those which do not also have a vibratory element conjoined thereto.

In certain embodiments, electrical contacts and/or connections connect the sensor means for determining the frequency of oscillation to an external control unit. Typically the piezoelectric actuator and piezoelectric sensor elements are insulated from the liquid which is present in the reaction chamber.

In certain embodiments the device of this aspect of the invention comprises at least beam members which are present within the reaction chamber. The reaction chamber defines a fixed volume which is suitable for receiving and retaining a fluid sample of which the density and/or viscosity is to be determined, or wherein changes in the density and/or viscosity of the fluid are to be measured. Typically, the at least 2 resonating beam members are positioned within the reaction chamber such that said beam members are brought into contact with a fluid sample when it is loaded into the reaction chamber. Typically, the reaction chamber functions to receive and retain the fluid sample in order that analysis of the sample can be performed, most specifically the determination of the density and/or viscosity of the sample. The analysis of the density or viscosity of the liquid can be performed at a fixed time point, or can comprises a series of readings which allows for the dynamic measurement of the progress of a biochemical reaction in which the liquid is involved.

As used herein, the term 'reaction chamber' may also be referred to herein interchangeably as a reaction cell.

In certain embodiments, the sensor device comprises further elements which serve to define the structural components of the reaction chamber about the at least 2 beam members. The reaction chamber defines an internal volume which receives and retains a fluid sample of which the density and/or viscosity is to be defined. The provision of the fluid sample into the reaction chamber allows the density and/or viscosity of the sample to be monitored by means of measurement of the oscillation of at least one of the at least 2 beam members.

In certain embodiments, the internal volume of the reaction chamber, which is defined about the at least 2 beam members, is defined by means of a plurality of layers, which may typically comprise the base substrate layer along with upper and lower substrate layers which are positioned above and below the planar face of the base substrate to provide a sandwich-type arrangement. Accordingly, in certain embodiments, the upper and lower substrate members are provided above and below the planar faces of the base substrate. Said upper and lower substrates provide for the formation of an area about the at least 2 beam members which is suitable to receive and retain fluid, this area is defined as the reaction chamber, that is, there is defined a volume suitable for receiving and retaining a fluid sample, such that the fluid sample is brought into contact with said at least 2 resonating beam members. The positioning and dimensions (in particular the thickness) of the upper and lower substrate members should be selected such that they do not impede the resonance or oscillation of the at least 2 beam members.

In certain embodiments, the upper and lower substrate layers may be comprised of a plurality of components which form each layer. Alternatively, the upper and lower substrate layers may comprise a plurality of sub-layers. The formation of the upper and lower substrate layers by a plurality of components allows for the shape of these layers to be altered or adjusted such that said layers can be position around and in a spatial relationship to the at least 2 beam members, but wherein this positioning does not result in the oscillation of the beam members being impeded. As such, in simple terms, the base and/or upper substrate is positioned about the resonating beam members in a manner which does not impede the oscillation of the beam members.

Furthermore, typically at least one of the upper and/or lower substrate members is shaped to allow for the formation of at least one channel and/or opening through which fluid can ingress into the reaction chamber. As such, said at least one channel and/or opening facilitates the entry of the fluid sample into the reaction chamber. In certain embodiments, the channel and opening are of suitable dimensions such that the fluid can enter into the reaction chamber by means of capillary action, capillarity or capillary motion.

In certain further embodiments, at least one of the formed channels and associated openings permits the outflow of air from the reaction chamber upon filling of the reaction chamber with the sample fluid.

In certain embodiments, the surfaces of the device which define the reaction chamber exhibit a low surface tension. In certain embodiments, the internal surface of the device is provided with a hydrophilic surface, said hydrophilic surface allowing the reaction chamber to be filled with fluid by means of a capillary action. In certain embodiments, the hydrophilic surface is disposed on a lid forming at least part of the reaction chamber.

In certain embodiments, the internal volume defined by the reaction chamber is typically less than about 100 ml (100 $cm^2$). In certain further embodiments, the internal volume defined by the reaction cell is equal to, or less than 1000 pl. The smaller the volume of the reaction chamber, the greater the surface area to volume ratio of the sample which is provided therein.

In certain embodiments, further layers may be provided about said upper and lower substrate layers in order to confer further strength and/or rigidity to the structure.

In certain further embodiments, the sensor device can be used to determine the density and/or viscosity of a fluid such as a biological fluid. In certain embodiments the biological fluid is blood, blood products or the like.

In certain aspects, the sensor device has utility in determining the levels of anti-coagulant in a blood sample or the like. In order to determine the presence and level of anti-coagulant within a blood sample, it is necessary to induce clotting. The clotting process, or haemostasis, is induced by clotting agents. In order to artificially induce haemostasis of the blood sample, at least one clotting factor must be added to the blood, or blood derived sample.

In certain embodiments, the device further provides a reagent comprising at least one clotting agent, said clotting agent being provided in an amount suitable to induce haemostasis of a blood sample.

In certain embodiments, the sensor device further comprises a reagent layer which comprises at least one clotting agent. In certain embodiments, said reagent layer comprises an effective amount of a clotting agent which is sufficient to induce haemostasis of a blood sample brought into contact with the device. In certain embodiments, the reagents present in the reagent layer are those required to perform a prothrombin test.

In certain embodiments the reagent layer is provided on the surface of the base substrate, and in particular, upon areas of the surface of the base substrate which are provided within reaction chamber. In further embodiments, the reagent layer is provided upon at least one of the beam members which are present within said reaction chamber.

In certain embodiments, the blood clotting agent(s) are provided as a reagent within the chamber which receives the fluid sample. In certain embodiments, the regent is provided upon the surface of at least one of the beam members. Typically the reagents include enzymes which induce an increase in viscosity, density and/or precipitation of the biological fluid (blood) sample. Reagents may be deposited on the inner surface of the reaction chamber, and are presented such that they rapidly dissolve and mix with the sample when it is introduced into the reaction chamber. Exposure of the body fluid sample to reagents causes a controlled reaction that causes the body fluid sample to coagulate.

In certain embodiments, the clotting agent is thromboplastin and/or calcium. A typical reagent used for this purpose is Manchester Capillary PT reagent (Hart Biologicals, Hartlepool, United Kingdom).

The invention further extends to an automated test meter which has utility in determining blood clotting time. In further aspects, the present invention extends to a sensor device of the first aspect of the present invention which can be brought into engagement with a test meter, in particular an electronic test meter which can provide automation with regard to the monitoring, processing and analysis of information derived from the sensor device of the invention. In certain embodiments, when provided in such a form, the sensor device of the invention may be a disposable test strip. The disposable test strip can be used in a test meter of the type that receives a disposable test strip and a sample of body fluid and which performs an analysis of the sample to establish the blood clotting time.

In certain embodiments, the test meter is portable, and comprises a display unit. Typically the test meter outputs the results in a visual form. Such a device could be used to measure coagulation of the sample itself or a physical change in a reagent due to species within the sample. An example of an application where coagulation might need to be measured is in management of anti-clotting therapy.

A yet further aspect of the present invention provides a method for accurately loading a fluid sample into a reaction chamber in order to determine at least one property of said fluid, the method comprising the step of providing at least one channel which permits fluid movement into the reaction chamber wherein the channel is of suitable dimensions such that it permits the ingress of the sample through the channel into the reaction cell by means of capillarity.

In various further aspects, the present invention extends to methods for determining fluid density and/or viscosity. The determination of resonant frequency is a more direct function of density than quality factor (Q-factor) which is more related to the viscosity of the fluid.

Accordingly, a yet further aspect of the invention provides a method for determining the density and/or viscosity of a fluid, the method comprising the steps of:

providing a fluid sample, loading a reaction chamber of a sensor device according to the first aspect of the present invention with said sample, inducing the oscillation of at least one resonating beam member provided within said reaction chamber, determining the oscillation of at least one resonating beam member provided within the reaction chamber, and determining the density and/or viscosity of the fluid sample with reference to the frequency of oscillation of said second beam member.

In certain embodiments the method may further comprise the step of exposing the fluid sample to at least one compound or reagent which induces a change in density and/or viscosity of the fluid sample. The fluid sample may be exposed to the at least one reagent prior to being loaded into the reaction chamber. In an alternative embodiment, the fluid sample is brought into contact with the reagent after the fluid sample has been loaded into the reaction chamber.

In certain embodiments, the resonating beam members are completely immersed in the fluid sample which is provided into the reaction chamber.

Typically, changes in oscillation of the beam members relate to determined changes in at least one of (i) the resonant frequency, (ii) the amplitude, and (iii) the quality factor of the oscillation of the resonating beams.

In certain embodiments a change in resonant frequency is used to detect when the reaction chamber of the sensor is filled with fluid sample during the loading step. The time point where the sample is loaded can indicate the starting point of a reaction which may be performed within the fluid sample which is contained in the reaction chamber, in order to determine at least one property of the fluid sample such as viscosity or density.

In certain embodiments, the fluid is analysed in order to determine the presence and level of anti-coagulant factors in the blood. This is determined by providing blood sample and inducing clotting of the blood sample. The determination of the viscosity of the blood sample, or, more specifically, changes in the viscosity thereof, allows the level of anticoagulant in the blood to be determined as this will be inversely proportional to the time taken for blood clotting to occur.

The present invention is not limited to quantifying the presence of blood clotting factors in blood, it may be used to quantify any change of state of a fluid.

In further embodiments, the change in resonance or oscillation by a beam member can be used to determine the starting point of a chemical reaction. For example, a clotting factor may be provided to a blood sample prior to loading into the sample, or factors or reagents which induce blood clotting may be provided on at least one surface which defines the reaction chamber such that when said fluid sample is brought into contact with the reaction chamber, a chemical reaction commences.

In certain embodiments, a change in the amplitude of the oscillation of a resonating beam member is used to detect when the reaction chamber of the sensor is filled with a fluid sample. This measurement can also be used to determine the start point of the chemical reaction, as the fluid sample may be exposed to a reagent which is present in the reaction cell or within a coating present in a surface of the reaction cell.

In certain embodiments, changes in the resonant frequency of the oscillation of a beam member are used to measure the progress of a chemical reaction occurring in the fluid sample contained in the reaction cell.

In certain embodiments, changes in amplitude of oscillation of a beam member are used to measure the progress of a chemical reaction occurring in the fluid sample, particularly where the change chemical reaction results in a change in state of the fluid sample.

In certain embodiments, changes in the quality factor (Q-factor) of the beam members can be used to measure the progress of a chemical reaction occurring in the fluid sample.

In certain embodiments, the fluid sample is a blood sample, and the method can be used to determine the blood clotting time of the sample. In order to artificially induce blood clotting in order to provide an indication of the amount of anti-clotting agents in the blood, the sample must be exposed to reagents which induce blood clotting, for example, thromboplastin and calcium. As such, in embodiments wherein the method of this aspect of the invention is used to determine blood clotting time (in order to determine the amount of anti-coagulant present in a blood sample, and in turn a patient), the method further comprises the step of exposing the sample to at least one blood clotting agent, said agent being provided to the sample loaded into the reaction chamber.

Furthermore, as the clotting reaction results in a change in density and viscosity of the blood, this method can be used to obtain a series of measurements which can be used to monitor the time course over which clotting occurs. The rate at which clotting occurs can be indirectly correlated with the presence of anti-coagulating factors which are present in the blood sample, as these anti-coagulating factors serve to prevent the clotting (haemostasis) reaction.

Accordingly, in a yet further aspect of the invention there is provided a method of determining the level of anti-coagulants in a blood sample, the method comprising the steps of:

loading a reaction chamber comprising at least 2 beam members with said sample, oscillating a first beam member, bringing the blood sample into contact with a reagent which causes blood clotting, determining the oscillation of at least one second beam member, establishing the density of said blood sample by evaluation of the oscillation frequency of said at least second member, comparing said readings to a standard in order to determine the level of anti-coagulant in the blood sample.

In certain embodiments, the level of anti-coagulants which are determined as being present in a blood sample can be, based on the amount of sample provided, used to calculate the overall level of anti-coagulants in a patient. This value has utility in the clinical management of a patient who is receiving treatment with anti-coagulant therapies.

In certain embodiments, the reagent which allows induces the blood clotting reaction can be any suitable blood clotting reagent.

In certain embodiments, the standard clotting time value is normalised to an international standard to give an INR (Internationalised Normalised Ratio) value. The INR value can then be used to assist in the clinical management of the patient from which the sample is derived. The targets for patients presenting with conditions such as Pulmonary embolus and proximal deep vein thrombosis, for example would be an INR of around 2.5. Patients presenting with a prosthetic heart valve should have an INR value of around 3.5. An INR value that is 0.5 above or below the target value indicates unsatisfactory dosage of therapeutic anti-coagulant(s).

Typically, changes in oscillation of a beam member relate to determined changes in at least one of (i) the resonant frequency, (ii) the amplitude, and (iii) the quality factor of the oscillation of the resonating beam member(s).

In certain embodiments a change in resonant frequency is used to detect when the reaction chamber of the sensor is filled with the blood sample. This can also be used to determine the start point of the coagulation chemical reaction.

In certain embodiments, a change in amplitude is used to detect when the reaction chamber of the sensor is filled with the fluid sample. This can also be used to determine the start point of the coagulation chemical reaction where the fluid is blood or a blood derived product.

In certain embodiments, changes in the resonant frequency are used to measure the progress of the coagulation chemical reaction occurring in the blood sample.

In certain embodiments, changes in amplitude are used to measure the progress of the coagulation chemical reaction occurring in the blood sample.

In certain embodiments, changes in the quality factor of the beam members can be used to measure the progress of the coagulation chemical reaction occurring in the blood sample.

In certain embodiments, a plurality of readings are obtained over a time course which commences upon entry of the blood sample into the reaction chamber, this series of readings being used to determine the progression of the blood clotting reaction. A fast rate of clotting indicates relatively low levels of anti-coagulant in the blood sample, whereas a slow rate of clotting indicates a high level of anti-coagulants in the blood sample. In relation to a patient at risk of a condition such as thrombosis, it is preferable to manage the risk of this condition by the provision of anti-coagulant drugs. However, the administration of too high a level of anti-coagulant drugs is undesirable as this could prevent blood clotting in the event of haemorrhaging.

In certain embodiments, the readings of beam member oscillation may be taken prior to, during or after the coagulation reaction. In further embodiments, the reading may be taken from at least two of before, during or after the coagulation reaction.

Following the filling of the reaction chamber with the blood sample, the clotting reaction can be initiated by the exposure of the blood sample to clotting agents.

In certain embodiments, the method further comprises the step of bringing the blood sample into contact with at least one clotting agent. The sample may be exposed to the clotting agent prior to loading the reaction chamber. Alternatively, reagents which induce a chemical reaction, such as blood clotting, can be added to the fluid sample once it is loaded into the reaction chamber.

In certain embodiments, the blood sample is brought into contact with the at least one clotting agent within the reaction chamber. In certain embodiments, the clotting agent is provided within a reagent layer provided on at least one surface of the reaction chamber. The reagent layer is positioned such that upon filling of the reaction chamber with the blood sample, the reagent layer is brought into contact with the blood sample.

Accordingly, in certain embodiments, the blood clotting agent(s) are provided as a reagent within the chamber which receives the fluid sample.

In certain embodiments, the reagent is provided upon the surface of at least one of the beam members, and/or upon at least one further surface which defines the reaction chamber.

Typically the reagents include enzymes which induce precipitation of the biological fluid sample, which may be a blood sample, or the like.

In certain further embodiments, the invention extends to the use of the device and methods of the present invention in the determination of the density and viscosity of a fluid sample.

According to a yet further aspect of the present invention, there is provide the use of a sensor device as defined herein for determining the density and/or viscosity of a fluid sample.

According to a yet further aspect of the present invention, there is provided the use of a device according to the present invention in the determination of blood clotting time.

According to a yet further aspect of the invention, there is provided the use of a sensor device as defined herein for determining the level of anticoagulant in a blood sample.

In certain further aspects, the present invention provides a kit for determining blood clotting time and/or determining the level of anti-coagulants in a blood sample, the kit comprising a sensor device according to the invention along with instructions for the use of the same and the provision of appropriate reagents.

In various further aspects, the invention provides a means for determining the level of haematocrit present in a sample. The determination of haematocrit (red blood cell levels) in a sample may effect the results obtained in the methods of the invention which are concerned with determining the clotting time of blood, or a related fluid, as a sample containing a high level of haematocrit will comprise less water, and accordingly, the reagents which are provided in order to artificially induce blood clotting would become solvent over a longer period of time as less water is available in the sample. As such the determination of the presence of haematocrit in a sample can be of utility in improving the accuracy of a test which determines blood clotting time in order to allow a determination of anti-coagulant levels.

The determination of haematocrit levels in a fluid (blood) sample has the further advantage that the initial determination of the presence and/or levels of haematocrit in a sample can be used to distinguish between 2 samples which differ in their material particulars. For example, if a set of standard plasma samples are used to calibrate an apparatus of the invention, then the apparatus, through the determination of the presence and/or level of haematocrit can confirm that the sample which is being tested is a patient blood sample, as opposed to, for example, a fluid sample which may be used to calibrate a device or confirm the oscillation of a beam member in a fluid of a defined density or viscosity.

Determining the presence of haematocrit in a sample would therefore provide a mechanism for reducing the error margin which may affect the accuracy and precision of the density and/or viscosity determination of a sample which is assessed using the methods of the invention which allow continuous density measurement.

Accordingly, in certain embodiments the methods of the invention may further comprise the step of determining the presence and/or level of haematocrit in a sample, prior to determining the density and/or viscosity of said sample.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As herein defined, the term 'quality factor' is a measure of the quality of a resonant system; specifically it is a measure of the sharpness of resonance or frequency selectivity of a resonant vibratory system. In all resonating devices, the quality factor is affected by the surroundings. The quality factor of a resonant system changes according to the viscosity of the media in which it oscillates. Accordingly, as the fluid becomes more viscous, this results in an associated change in the quality factor of the fundamental resonance of the resonating beam structures described herein.

As herein defined, the terms "resonance phase angle" relates to a measurement of the difference in phase of the resonance of one resonating beam relative to the phase of a second resonating beam.

As herein defined, the terms "resonance frequency" means the frequency when a material, in this case a resonating beam structure, resonates at maximum amplitude for a specific mode of resonance. The frequency of the resonating beam will change relative to the viscosity of the fluid in which it is immersed. In one aspect, the invention therefore provides a viscometer which comprises at least one resonating beam, where the frequency of the vibrational beam allows a change in viscosity of the fluid to be determined. Hence, the frequency of the resonating beam as which is detected may not always be the resonant frequency.

In certain embodiments, the determination of the change in density and/or viscosity is performed by continually monitoring the density or viscosity of the sample mixture. Such continuous monitoring may be referred to as dynamic monitoring of the density or viscosity of the fluid mixture. Accordingly, in certain embodiments, the method of this aspect of the invention allows the rate of change of density and/or viscosity of a sample mixture to be measured.

In certain embodiments, the determination of the change in density or viscosity of the sample mixture may be determined by the taking of a series of readings relating to determining the parameter of at least one of resonance frequency, resonance phase angle and/or quality factor, said readings being spaced out over a series of determined time points, wherein the data obtained from said readings can be analysed in order to determine any resulting change in the density and/or viscosity of the fluid sample.

In certain embodiments, the data relating to at least one parameter which is derived from the resonance of the resonating beam member may processed, for example, using an algorithm, in order to determine whether there has been a resulting increase in density of the sample mixture. Accordingly, in various further aspects, the invention extends to an algorithm, and further to the use of an algorithm for processing data in order to provide a numerical value which can be used in the determination of the density and/or viscosity of a fluid sample.

In certain embodiments, the data relating to the at least one parameter which is determined from the at least one resonating beam member can be compared to known values in order to determine whether there has been an associated increase in density and/or viscosity of the sample mixture.

In certain embodiments, the analysis of the data obtained in relation to the at least one parameter is performed locally at the site of performance of the reaction. In certain embodiments, the data obtained in relation to the at least one parameter is communicated to an analysis apparatus which is located remotely to the apparatus used to perform the reaction in order to determine any change in density and/or viscosity of the sample mixture.

In certain embodiments, an increase in the density and/or viscosity of the sample mixture can be determined by detecting a reduction in the resonating frequency of the resonating beam member. The determination of resonant frequency is a more direct function of density than quality factor (Q-factor) which is more related to the viscosity of the fluid.

In certain embodiments, an increase in the density and/or viscosity of the sample mixture can be determined by detecting a variation in the quality factor (Q factor), typically an increase in the quality factor. In certain embodiments, a measurement of the rate of change of Q factor is used to determine the rate of change of liquid viscosity.

In certain embodiments, an increase in the density and/or viscosity of the sample mixture can be determined by detecting an alteration in the resonance phase angle of at least one resonant beam relative to at least one further resonant beam.

Typically an increase in the density and/or viscosity of the sample mixture illustrates that the sample mixture is undergoing gelation or coagulation.

As used herein, terms such as "a", "an" and "the" include singular and plural referents unless the context clearly demands otherwise. Thus, for example, reference to "an active agent" or "a pharmacologically active agent" includes a single active agent as well two or more different active agents in combination, while references to "a carrier" includes mixtures of two or more carriers as well as a single carrier, and the like.

Figure 1A:
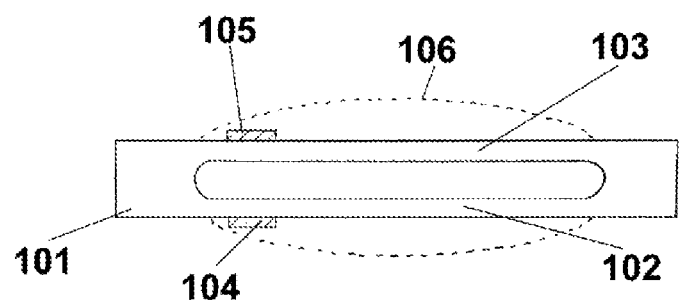
FIG. 1(A) and FIG. 1(B) depicts schematically two embodiments of a resonant beam member assembly which are suitable for measuring properties of a fluid before, during and after a chemical reaction within that fluid, with FIG. 1(A) showing a two beam resonant assembly arrangement, and FIG. 1(B) showing a three beam resonant assembly arrangement, with the beams positioned at two resonant nodes.

The present invention will now be described with reference to the following examples which are provided for the purpose of illustration and are not intended to be construed as being limiting on the present invention.

DETAILED DESCRIPTION OF THE INVENTION

Without wishing to be bound by theory, the present inventor predicts that the determination of fluid viscosity is achieved by determining the resonance of an oscillating beam member. The principle of resonance may be further defined with respect to the function of a tuning fork.

When a tuning fork is excited by striking it against a surface or an object, its tines or resonating beams resonate at a certain frequency known as the fundamental frequency. The fundamental frequency of the tines is dependent on the length, and cross-sectional area of the tine as well as the material from which the fork is made. This can be further determined using Formula I as set forth below:

$f_0 = (a2/2\pi 12)*(El/ps)0.5$

In this formula, fo is the fundamental or natural frequency; E is the Young's modulus of the material; s is the cross-sectional area of the tine or resonant beam; I is the length of the beam; I is the second moment of the cross-sectional area; a is the value determined by the node; p is the density of the material.

The tines (or prongs) of tuning forks can be joined at either one end or both ends. The resonating beam members of the invention apply the principles of a tuning fork tine, with the resonating beams being joined at each end, thus acting as a double-ended tuning fork. The benefit over using a single ended tuning fork, cantilever sensor or piezoelectric crystal (cut to provide surface acoustic waves) is that the damping forces resulting from the fixture of the resonant structures are lower in a double ended tuning fork.

The density of a body fluid can be determined by comparing the resonant beam fundamental frequency in air with the fundamental frequency when the sample has been received by the reaction chamber. A further benefit of the resonating beam over a device based on a piezoelectric crystal (cut to provide surface acoustic waves) is that the amplitude of the resonant beam is larger and this amplitude is very sensitive to the density and viscosity of the surrounding medium.

As herein defined, the quality factor (Q-factor) is a measurement of the "quality" of a resonant system; it is a measure of the sharpness of resonance or frequency selectivity of a resonant vibratory system. In all resonating devices, the quality factor is affected by the surroundings, in the case of the present invention, the surroundings of the beam member. The quality factor of a resonant system changes according to the viscosity of the media in which it oscillates. However, in a double-ended tuning fork device, the quality factor is significantly higher than in piezoelectric devices, giving a much wider dynamic range which allows a single sensor to provide measurement in both air and body fluids that change viscosity during a chemical reaction. The amplitude of the resonant beam is proportional to the body viscosity; in a low viscosity fluid, a resonant beam will oscillate with much higher amplitude over a narrow frequency about its fundamental, compared to a resonant beam in a high viscosity fluid. Introduction of a fluid sample into the reaction chamber causes damping of the resonating beams, changes in frequency and quality factor of the resonating beam indicates blood coagulation.

The resonating beams are further dampened by the increasing viscosity of the fluid sample as it coagulates; this damping effect being measured periodically to determine the coagulation of the body fluid as a function of time.

The walls of the reaction chamber may be positioned closely together to form a capillary. The materials chosen to create the surfaces of the reaction chamber is selected to provide a low surface tension which allows the reaction chamber to fill by a capillary action. These materials are selected as they enhance liquid filling without interfering with the reaction. Examples of such materials will be well known to the person skilled in the art.

Upon complete filling of the reaction vessel, any changes in quality factor and frequency will momentarily stabilise, before further changes take place due to the chemical reaction. The fast response time of the sensor allows for the accurate identification of the time at which the body fluid sample was introduced to the reaction chamber. Alternatively a set of electrodes could be introduced into the reaction chamber such that when the fluid enters the chamber, electrical contact can be made.

The resonating beams are formed within a sensor element that can be of any suitable inert material and may be selected from amongst others: silicon, gold, platinum or steel. The resonating beams can be formed by etching, laser treatment or by mechanical punching of the base substrate. The benefit of using resonant members joined at both ends is that damping forces due to the mounting of the resonant members are essentially cancelled out and thus do not feature in the sensor response. The resonating beams are excited and monitored by means of piezoelectric elements that may be located outside of the reaction chamber. This is a particular benefit as piezoelectric elements are highly sensitive to changes in temperature.

Electrical connections are made to these piezoelectric elements by means of patterned conductive layers that form circuits. The conductive circuits can be of any suitable conductive material and may be selected from, but not limited to: gold, platinum, copper or silver. The conductive layers can be patterned by several methods such as laser ablation, or by screen printing. The conductive layers would serve to connect the piezoelectric elements to the edge of the sensor element. In certain embodiments, a series of edge connectors could be provided to allow direct contact or connection between a test meter and the piezoelectric elements.

An additional purpose of the conductive circuit would be to activate the device in readiness to receive a sample, by means of bridging contacts provided by the edge connectors. Alternatively, the piezoelectric elements could be excited and/or monitored by non-contact means such as microwave amplitude reflection, light beams or radio frequency.

The separate layers of the test strip could be aligned such that no further trimming or adjustment to their size and/or outer peripheral surface would be necessary. However, a plurality of devices could be produced and trimmed to the desired size and shape of the disposable test strip.

Monitoring or reading of the sensor device in order to provide an automated means for determining the density and/or viscosity of a fluid sample can be provided by the use of a machine, such as a metering device, which can interact with the sensor device of the invention in a manner which allows for the meter to determine the results of the sample testing.

In an embodiment where the sensor device is connected to, or engaged with a meter, this provides an automated means for determining the density or viscosity of a fluid. For example, where the meter is connected to the sensor device, the meter could be releasably engagable with the test strip and would have the ability to output the test results, typically by means of a visual display or readout. In addition, where the meter processes the data received from the sensor device, the meter may process this information and apply correction factors which would take into account any batch to batch variability associated with the disposable test strip manufacture.

Additionally, the meter may include a facility to sample environmental conditions such as temperature and apply a correction factor to the measurement response. Additionally the meter would have a memory facility that would allow previous readings to be stored and recalled, for example to provide a comparison of date. This feature may be of particular utility to an individual whom undergoes regular testing as part of the monitoring of anti-coagulant levels in the blood.

In order to calibrate the machine or the individual sensor device, the meter may perform an initial self-test on the disposable strip prior to blood introduction.

Figure 1B:
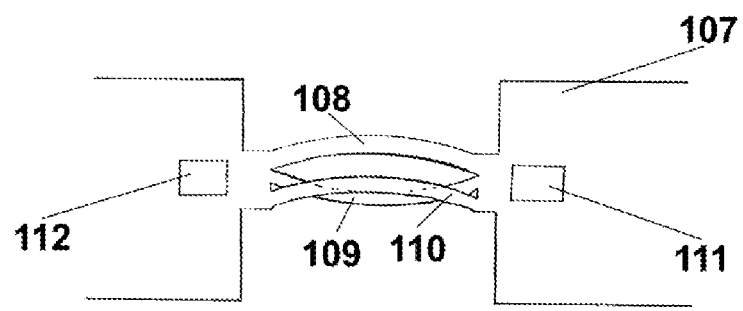

FIG. 1(A) and FIG. 1(B) show two embodiments of the sensor devices of the invention which contain resonant beam member structures, the oscillation of which is used to determine the viscosity of a fluid, typically a liquid.

The first embodiment, as shown in FIG. 1(A), comprises a substrate 101 which has been machined to form two resonating beam structures (or tines) 102 and 103, the beam structures being attached to the main body of the base substrate at each of their longitudinal ends. One such beam member 103 is conjoined to a first piezoelectric element 104, which in operation causes the beam to oscillate at its fundamental frequency, or at a harmonic frequency.

A second beam member 102, which is substantially identical to the first beam member 102, oscillates in harmony with the first beam 103, and has a second piezoelectric "pickup" sensor element 105 conjoined thereto.

This second piezoelectric "pickup" sensor element 105 converts the physical oscillatory movement of the second beam member into a measurable signal, typically an electrical output. The oscillation nodes of the beam members are indicated by the dotted line 106. The shape and geometry of the resonant beam members 102 and 103, and the exact location of the piezoelectric elements 104 and 105 conjoined thereto may be selected to obtain the optimum sensitivity of detection of changes in fluid viscosity.

In the embodiment of the sensor device shown in FIG. 1(b), an alternative triple beam arrangement is provided. A base substrate 107 has been machined to form three resonating beam structures 108, 109, 110. A first piezoelectric drive element 111 (also known as a vibration excitory device) is provided on the base substrate, this being disposed proximally to the longitudinal ends of the three resonating beam structures. The three resonating beam structures are depicted at one oscillation node that would occur when the structure is driven by element 111. The oscillation of beam members 108 and 110 move in substantially the same sequence, while beam member 109 moves in the same plane, but with a different sequence of movement. A second piezoelectric "pickup" sensor element 112 is provided upon the base substrate 107 at a position proximal to the longitudinal ends of the beam members 108, 109, 110 which is at the opposing end of the beam members which are proximal to where the vibration excitory element is positioned, in this case the first piezoelectric drive element 111. The piezoelectric "pickup" sensor element 112 converts the physical movement of the second beam into a measurable signal, typically an electrical output which can be processed by a meter in order to determine an output value or reading.

Figure 2B:
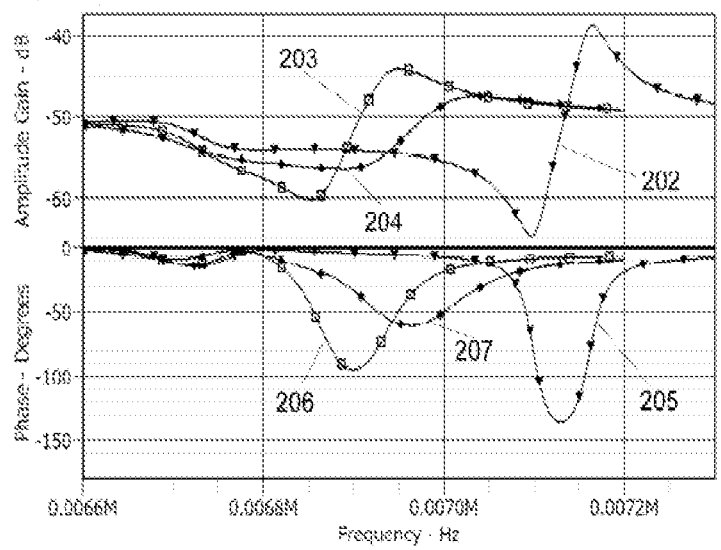
FIG. 2(A) and FIG. 2(B) are graphs showing the typical sensor response of a resonant beam assembly which is suitable for measuring properties of a body fluid before and during a chemical reaction.
Figure 2A:
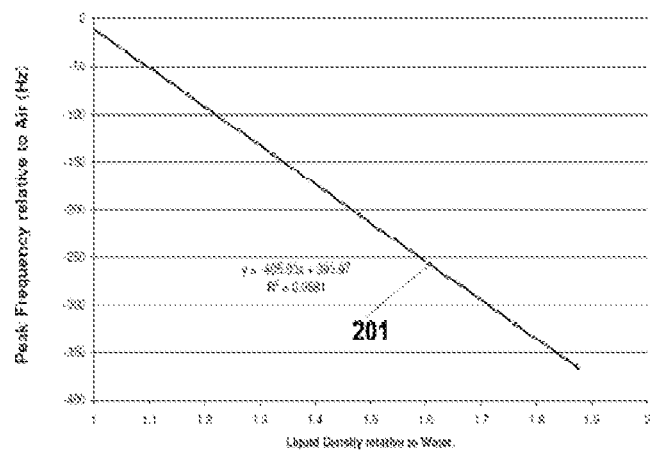

FIG. 2(A) and FIG. 2(B) shows graphs depicting the sensor responses of a resonant beam assembly suitable for measuring properties of a body fluid before and during a chemical reaction. In particular, FIG. 2(A) depicts the changes in natural frequency of the resonant beam assembly with respect to fluid density 201.

FIG. 2(B) depicts changes in amplitude and phase with respect to solution viscosity.

The response curve 202 relates to the amplitude of a resonant beam assembly oscillating in air; 203 relates to the amplitude of a resonant beam assembly oscillating in a freshly sampled blood drop; 204 relates to the amplitude of a resonant beam assembly oscillating in a coagulated sample. One skilled in the art could calculate the quality factor by measuring the frequency of the peak amplitude divided by the width of the response at half the amplitude. The response curve 205 relates to the phase difference between the tines of the resonant beam assembly oscillating in air; 206 relates to the phase difference between the tines of a resonant beam assembly oscillating in a fresh blood drop; 207 relates to the amplitude of a resonant beam assembly oscillating in a coagulated sample.

Figure 3A:
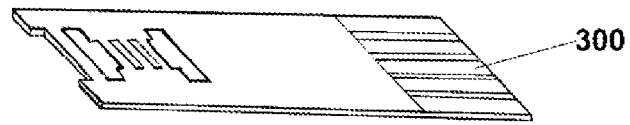
FIG. 3(A) depicts schematically an embodiment of a resonant beam sensing unit, FIG. 3(B) showing an exploded view of a resonant beam sensing unit that illustrates the component layers which contribute thereto.
Figure 3B:
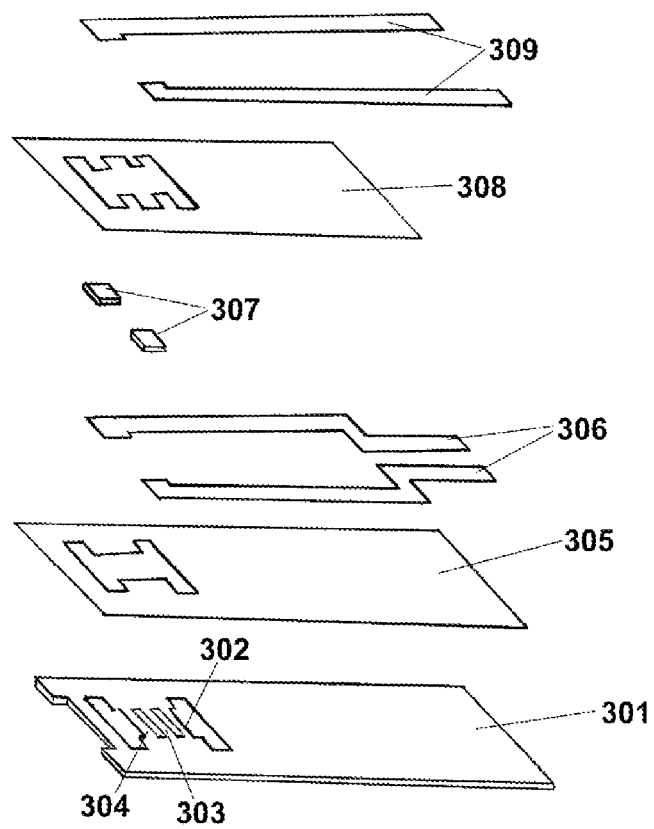

FIG. 3(A) and FIG. 3(B) shows embodiments of a resonant beam structure which is suitable for measuring properties of a fluid, in particular a body fluid, before and during a chemical reaction. As shown in FIG. 3(A), there is provided a triple beam resonant sensor assembly 300 for integration into a disposable test strip embodiment of the sensor device of the invention.

FIG. 3(A) shows an exploded schematic of a triple beam resonant sensor assembly for integration into a disposable test strip. A base substrate 301 is patterned with three resonant beam structures 302, 303, and 304. These beam structures may be formed by any conventional method such as laser or chemical etching or by stamping of the base substrate. A patterned insulating dielectric layer 305 is disposed onto the base substrate 301. The patterned insulating dielectric layer may be disposed thereon by any conventional method such as screen printing or ink jet printing. Alternatively, a pre-cast film may be laminated over the base substrate 301.

Patterned conductive tracks 306 are disposed on the patterned insulating dielectric layer 305. These conductive tracks may be disposed by any conventional method such as screen printing or ink jet printing and can be composed of any suitably conductive and chemically inert material.

A pair of piezoelectric elements 307 are disposed onto the patterned conductive tracks 306, at a location which is in close proximity to the central resonant beam 303. A second patterned insulating dielectric layer 308 is disposed to cover the majority of the patterned conductive tracks 306. The second dielectric layer 308 is shorter in length at the end distal to the beams in order to expose the ends of the conductive tracks 306. The second patterned insulating dielectric layer 308 may be disposed by any conventional method such as, but not limited to screen printing or ink jet printing. The second patterned insulating dielectric layer 308 functions to cover the conductive tracks 306 in order to allow the printing of a further conductive track (shown in this embodiments as feature 309) upon this layer. Accordingly, a second set of patterned conductive tracks 309 are disposed over the second patterned insulating dielectric layer 308 and the piezoelectric elements.

The patterned conductive tracks 306 and 309 may run the length of the base substrate 301, as shown in FIG. 3(A), such that an electrical connection can be made between the piezoelectric elements 307 and an external device, such as a meter, by means of any suitable connector (not shown).

Figure 4A:
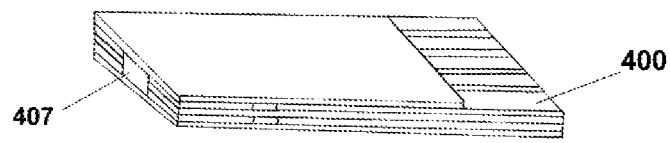
FIG. 4(A) shows a schematic view of a test strip for use in determining the coagulation of a blood fluid sample.
Figure 4B:
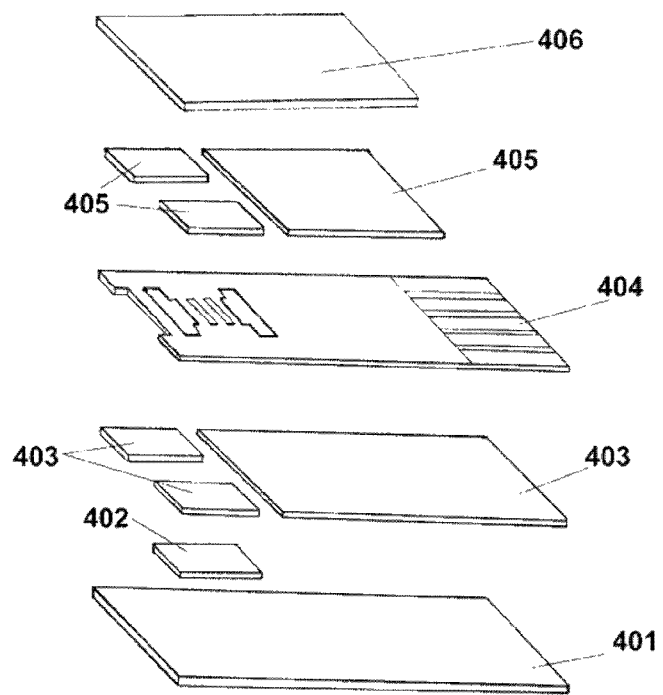
FIG. 4(B) shows an exploded view of a test strip which illustrates the components therein.

FIG. 4(A) and FIG. 4(B) illustrate a further embodiment. FIG. 4(A) shows a further embodiment of a sensor device in the form of a disposable test strip 400.

FIG. 4(B) shows an exploded schematic of the disposable test strip 400 of FIG. 4(A). The disposable test strip 400 comprises, a base substrate 401 onto which is disposed a reagent layer 402. Alternatively the reagent layer 402 could be provided upon any internal surface of the reaction chamber.

A first chamber forming layer 403 is disposed onto the base substrate 401. This chamber forming layer may be formed using a patterned pre-cast film, or by screening printing or ink jet printing a suitable non-reactive polymeric material. A resonant assembly 404, such as that previously detailed in the embodiment depicted in FIG. 3(A) and FIG. 3(B) may be laminated over the first chamber forming layer 403.

A second chamber forming layer 405 is disposed over the resonant assembly 404. A polymeric film 406 is then laminated onto the top of the second chamber forming layer 405. The purpose of film 406 is to provide an upper seal layer on the reaction vessel and to protect the underlying structures of the remainder of the test strip from mechanical damage. The film 405 further improves the stiffness of the disposable test strip.

The structure and arrangement of the elements of the first chamber forming layer 403 may comprise two or more subsidiary pads arranged in relation to the main body of the first chamber forming layer 403 in order to define an opening which allows a sample of fluid to be loaded into the chamber, which is defined by an internal volume provided within the sensor device. The fluid may be a body fluid, for example blood. The arrangement of the two or more subsidiary pads which contribute to the first chamber forming layer 403, may be arranged in relation to the main body of the first chamber forming layer 403 in order to further provide at least one further channel or opening, typically provided at a different side of the reaction chamber to the main opening, these secondary openings allowing for the side filling of liquids, or which, due to the opening being communicable with the central reaction chamber, also permit air to escape from the reaction chamber as it is loaded with a fluid sample.

In use, the test strip would be inserted into a testing meter, such that the contacts provided at the end of the test strip device (306 and 309 shown in FIG. 3(B)) opposite to the reaction chamber, would provide direct electrical connection to the piezoelectric elements. Insertion of the test strip into a testing meter would switch on the testing meter, and prepare the system to make a measurement. A small sample of body fluid may be provided either directly from a wound site, or alternatively the body fluid may be provided from a storage container or from an intermediate device such as a dropper which facilitates loading of the fluid into the reaction chamber.

A drop of fluid would be contacted with the opening channel which allows the fluid to enter into the main reaction chamber 407. Ingress of the fluid into the chamber through the opening and adjoining channel is typically facilitated by a capillary action, this capillary effect resulting from the dimensions and arrangement of the channel. Other factors, such as the materials used in the construction of the sensor device may facilitate movement of the fluid into the reaction chamber by capillary motion.

As fluid is drawn into the reaction chamber, the resulting change in the density of the regions around the resonant beam assembly results in changes in the oscillation of the beam members, this including the electronics commencing analysis of the body fluid sample. During a known time period, the analysis would be complete and the changes in viscosity and density of the fluid sample before and during the reaction would be measured. After a suitable reaction time has passed, an algorithm would be used to convert the natural frequency signal and the quality factor measured into a usable test result.

A further embodiment uses the piezoelectric polymer, polyvinylidene fluoride (PVDF) instead of the PZT layer for either or both actuator and resonator. PVDF has been used before to create closed loop sensors, in particular a "singing" tube and plate. Energy is applied to the system using as actuator component made from PVDF and that energy is then modulated by a signal measured by a receiver component made of PVDF.

In this embodiment the PVDF would be die-cut into a suitable shape to fit a resonator. As the PVDF is a dielectric material, the PVDF polymer can be used as a substrate onto which electrically conductive tracks are deposited. This embodiment further allows for the use of a dielectric, pressure sensitive adhesive to assist in laminating the cut and patterned PVDF film onto the resonator.

A thin metal sheet (for example 316 S11 annealed stainless steel foil) up to 500 um thick would be patterned such that is has multiple resonating beam structures joined at both ends. Other stainless steels, inert metals and alloys can be used depending on the application required. This patterning can be achieved using photolithography, laser ablation cutting, wire cutting, water cutting or mechanical punching as known by anyone skilled in the art. The dimensions of the beam are important, the width of the centre beam must be exactly twice the width of the two outer beams.

A portion of PVDF film (such as manufactured by Measurement Specialties, Inc, USA) would be prepared with electrodes and conductive tracks on both sides. These patterns would be made from a conductive material, for example but not limited to gold, silver, platinum, carbon mixed with conductive metals, indium tin oxide. This material would be formulated for deposition as an ink (such as sold by Dupont) or solid material would be sputtered (plasma) or evaporated on the surface. These patterns would be created as known by any anyone skilled in the art; by printing a thick film, by vacuum metallisation through a mask, by vacuum metallisation and subsequent photolithography. The design of the patterns would be such that the actuator and measurement areas of the PVDF film would be sandwiched by the conductive films. The remaining area of the PVDF acts as a substrate for conductor tracks. Conductor tracks would be designed to carry signals from the actuator and measurement parts to a convenient edge of the PVDF portion, where a connection to an external measuring device can be made.

The prepared portion of PVDF film would now be aligned and laminated onto the multiple beam resonator structures. Special marks might be used to ensure that the area of PVDF sandwiched align with the node areas on the triple beam device. The PVDF film is laminated to the multiple beam resonant structure by using acrylic pressure sensitive adhesive such as that sold by Apollo Adhesives (Tamworth, Staffs), using heat, using pressure, using ultrasonic welding techniques (Stapla, Mass. USA) or a combination of any of these.

Figure 5A:
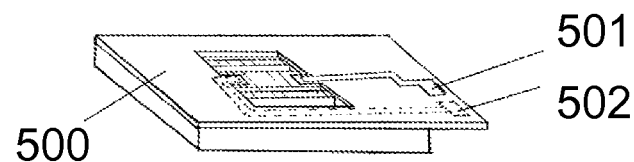
FIG. 5(A) shows a schematic view of an alternative embodiment of a sensor device according to the present invention wherein the sensor has a triple beam resonator with piezoelectric elements which is formed using a PVDF film.
Figure 5B:
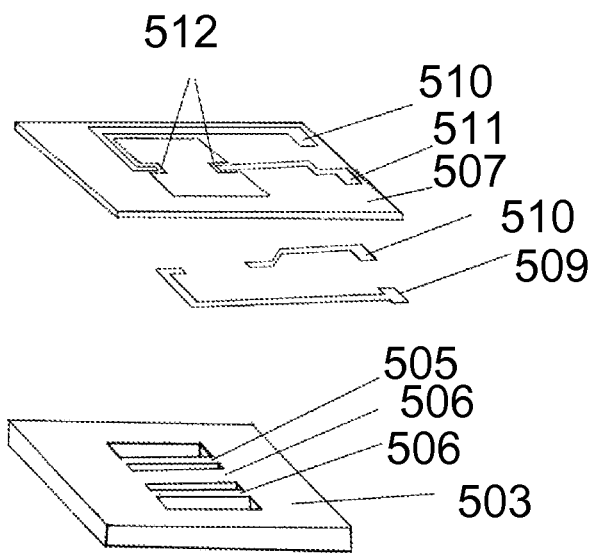
FIG. 5(B) shows the sensor device of FIG. 5(A) in an exploded view.

FIG. 5(A) and FIG. 5(B) provide examples of a triple beam resonator made as described in this embodiment. FIG. 5(A) provides a partially completed sensor 500 with the electrical connections 501 (top right connection), and 502 (underside bottom left connection) and the sample analysis window 503. The top left and bottom right connections are not shown here. FIG. 5(B) provides an exploded view of the individual layers that make up the completed sensor 500. The patterned steel substrate 503, has three resonant structures; centre beam 504, and a left beam 505 and a right beam 506. The patterned and die-cut PVDF film 507 is aligned carefully over the steel structure 503. The PVDF is patterned on two sides with conductive layers 508 and 509 on the underside, and conductive layers 510 and 511 on the topside. The conductive layers are so disposed to form a sandwich (i.e. conductive-dielectric-conductive) at the nodes of the resonator, 512. The conductive layers are also disposed such that a convenient access to the tracks can be obtained at the edge.

EXAMPLES

Example 1

Determining the Clotting Characteristics of Human Blood Using a Triple Beam Resonance Sensor Materials and Methods:
The following instrumentation was used:
(i) Cypher Instruments C60 Network Analyser, (ii) 0.0001 g Balance Type AE 100-S (Ring Mettler Instruments Ltd.), (iii) Ultrasonic bath U50 (Ultrawave Limited) (iv) Fibrinotherm and Custom Faraday Chamber (Highland Biosciences Ltd, Inverness, UK), and (iv) 0.1° C. Thermometer Hydrus 400 of Fisherbrand (accuracy 0.1° C.).

The following materials were used in this example:

PZT Crystals (PI Ltd., Dunstable, UK.), Silver Epoxy Resin (RS Components, UK), Fine copper wire (RS Components, UK), household Sugar (Tate and Lyle), Manchester Capillary Prothrombin Time Test Kit—HB1133 FG (Hart Biologicals, Hartlepool, TS25 1TZ), rabbit Brain Thromboplastin, processed Sheep Plasma, calibrated Reference Plasma: 250407-N. INR Value 0.95, 051206-L1. INR Value 2.4, and 180506-L2. INR value 4.0, human blood from two anonymous donors.

The resonator device was constructed as follows:

Sheet stainless steel 316 was annealed and then photo etched to form a triple beam resonator. The dimensions of the structure were defined by the photo etching process and were as follows: length of beam: 18 mm, width of centre beam: 2 mm, width of outer beam: 1 mm, gap (spacing) between the tines: 500 pm, estimated fundamental frequency 5181 Hz, material thickness: 250 pm.

A single PZT chip (of dimensions 2 mm×2 mm×1 mm) supplied pre-coated with aluminium on two faces is positioned on the central beam at the ends of the resonant modes. Connectivity was provided using a silver loaded epoxy adhesive and fine copper wires. The epoxy adhesive was applied to both faces of the PZT chip, and placed in position with the fine wire trace being held in place until the adhesive hardened. The adhesive was cured in an oven at 120° C. for 1 hour. Further curing for 24 hours at room temperature was required to allow the paste to completely harden.

Samples were prepared as follows:

Density and Viscosity

Sugar solutions of household cane sugar and deionised water at concentrations of 10% w/v, 20% w/v, 40% w/v, 70% w/v, 80% w/v were prepared. The solutions were produced in 10 ml deionised water and corresponding mass of sugar (measure with balance) for different sugar solution concentrations. Immersing the vessels in an ultrasonic bath for a few minutes improves the rate of dissolution.

Reference Plasma

The reference plasmas were prepared as per the manufacturers' instructions. Briefly, each sample was diluted using a physiological PBS buffer, and gently mixed to avoid frothing.

Blood Samples

Two volunteers presented 4 ml of venous blood into EDTA coated tubes. The blood was stored at 4° C. and warmed to 37° C. immediately prior to use.

The experimental procedure was performed as follows:

(i) Analysis of the Density and Viscosity Standards

The frequency analyser was configured and set to scan between 3300 and 5000 Hz, collecting 1024 data-points at a rate of 6 data points per second.

The density samples were analysed by measuring and recording the temperature of the samples. 60 µl of the sample was applied to the centre of the triple beam assembly, to an area relating to the reaction chamber (or reaction chamber) which covered all three beam members. This drop of liquid was then analysed to ensure that there were no air bubbles present in the sample. The faraday cage was then closed and the performance of the frequency scan commenced.

(ii) Preparation of the INR Calibration Curve and Analysis of the Samples

The frequency analyser was configured and set to scan between 3700 and 4100 Hz, collecting 120 data-points at a rate of 6 data points per second. This affords a scan time of 20 seconds.

The three plasma standards (L1, L2 and N) and blood samples were analysed using the following protocol:

100µ of reconstituted Manchester reagent was pipetted into an Epindorf tube. The liquid was heated to 37.4° C. The heated liquid was then left for 2 minutes. 20 ul of the plasma standard or blood sample was then added to the Manchester reagent. 60 µl of the mixture was immediately pipetted onto the triple beam sensor. The faraday cage was closed and the frequency scan commenced.

Results and Discussion (i) Performance of the Sensor in Air

Figure 6:
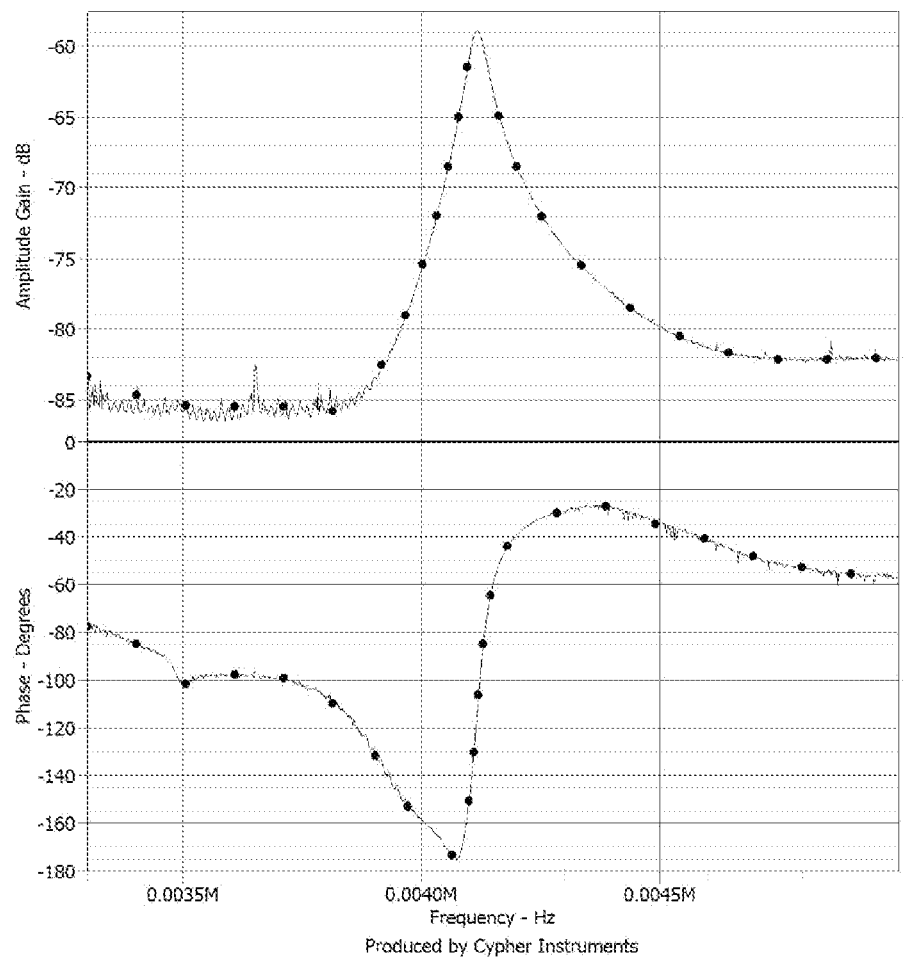
FIG. 6 shows a graph detailing the results of a single frequency scan of a triple beam sensor with air present in the reaction chamber, the frequency scan is of a beam member of a length of 18 mm between 3000 Hz and 5000 Hz.

An example of a scan in air is shown in FIG. 6. The sensor produces a resonant peak at 4095 Hz. The quality or Q-factor at −3 dB is 75. Some electrical noise is present; most is eliminated by the Faraday chamber. 10 repeats were made over 40 minutes and the following observations were made. The peak height ranged from −60.83 and −60.66 dB. The peak frequency ranged from 4090 to 4096 Hz.

(ii) Liquid Sensing Characteristics

Figure 7:
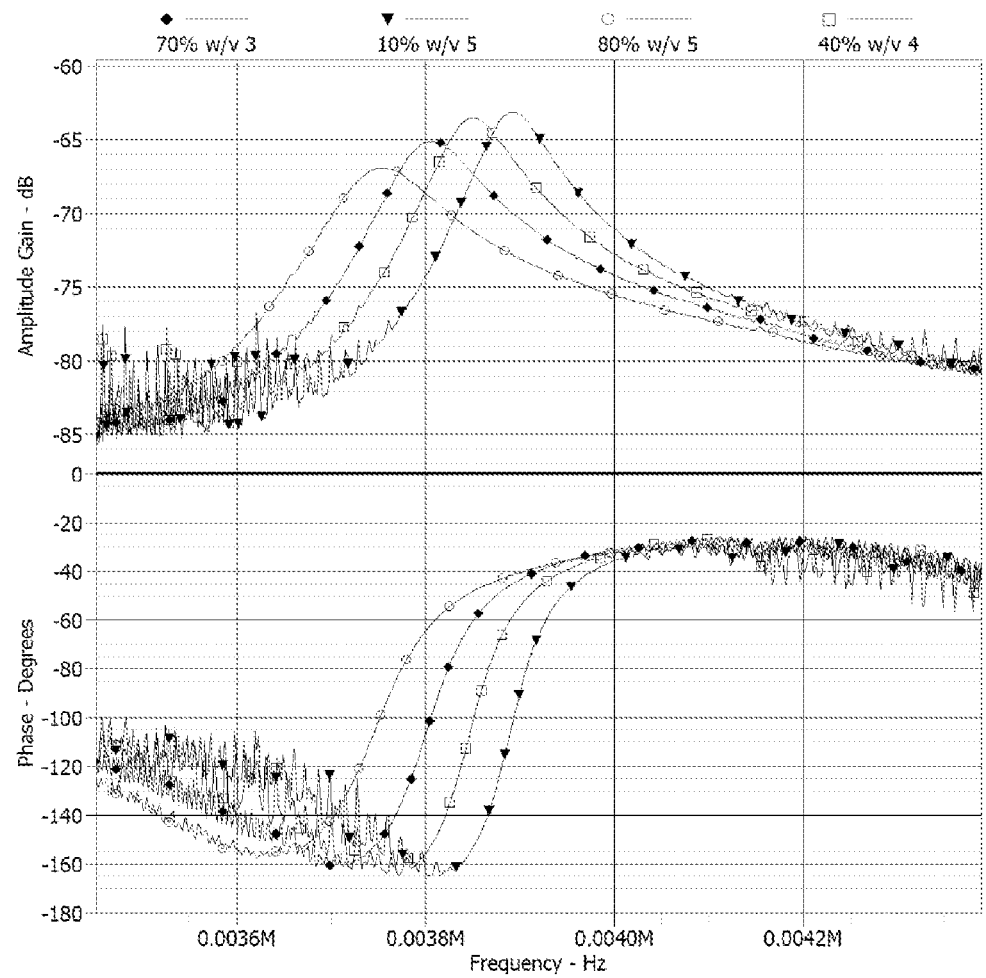
FIG. 7 shows a graph detailing the results of a scan of a range of solutions which contain sugar in different concentrations which are provided into the reaction chamber in order to determine how amplitude and frequency are affected by the viscosity and density of the liquid surrounding the triple beam assembly (sugar solutions of 10% w/v are illustrated by triangles, sugar solutions of 40% w/v are depicted by squares, sugar solutions of 70% w/v are depicted by diamonds and sugar solutions of 80% w/v are depicted by circles), FIG. 8(A)

The sugar solution offers a viscosity and density product for initial evaluation of the sensor performance. Raw data from a range of sugar concentrations is shown FIG. 7.

Increasing concentrations of sugar dampen the sensor, such that the amplitude decreases. As the solutions become more dense it causes the beams to move more slowly through the liquid and correspondingly the frequency decreases.

Figure 8A:
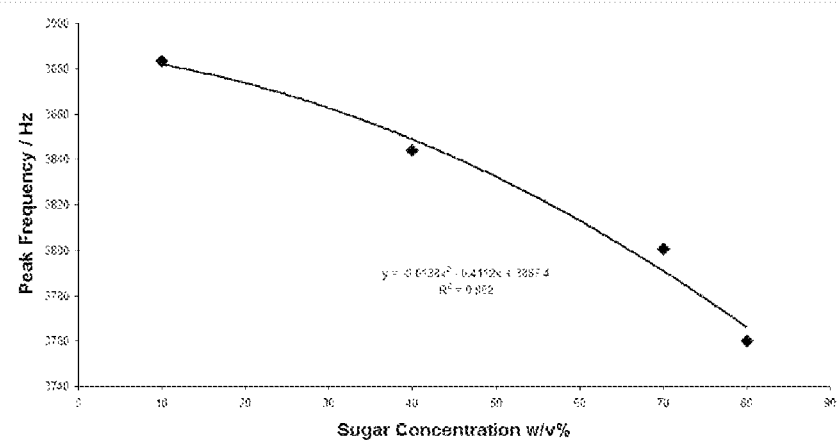
FIG. 8(B) shows two graphs illustrating the relationship between concentration and sensor response of frequency (FIG. 8(A)) and Q-factor (quality factor) (FIG. 8(B)) to sugar solutions in de-ionised water.
Figure 8B:
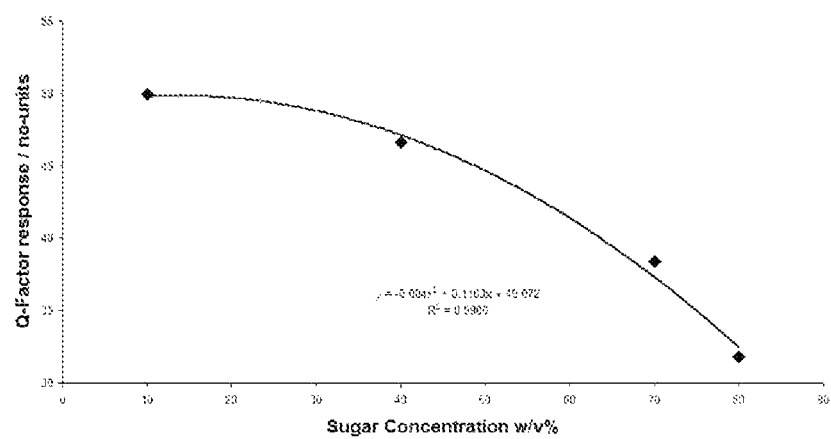

From analysis of the data from the study of the relationship between sugar concentration and frequency it was found that the data can be described by a polynomial. Plots of sugar concentration with respect to frequency and quality factor are shown in FIG. 8(A) and FIG. 8(B). This is expected as sugar not only changes the density, but it also changes the viscosity as shown in Table 1.

TABLE 1

The relationship between sugar concentration and viscosity/density.

| Sugar Concentration (w/v)[%] | Viscosity [mPas] | Density [g/cm$^3$] |
|---|---|---|
| 0 | 0.99 | 0.99 |
| 10 | 1.33 | 1.03 |
| 40 | 4.42 | 1.15 |
| 70 | 51.7 | 1.27 |
| 80 | 86.2 | 1.30 |

Preparation of the INR Calibration Curve

Figure 9:
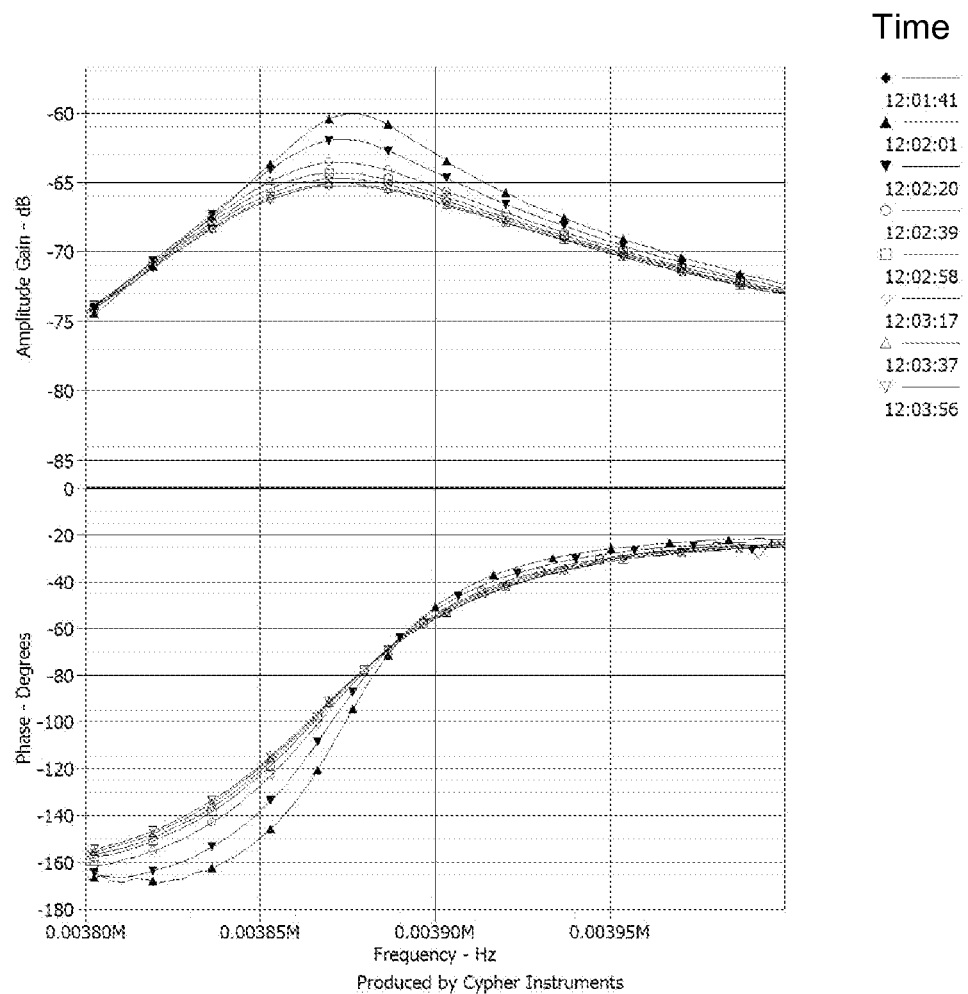
FIG. 9 shows a graph illustrating an example of a sensor response to a prothrombin clotting reaction to a standard plasma, with the sensor being scanned approximately every 20 seconds to follow the reaction with a plasma standard (INR 4)

The frequency response plots were analysed to obtain the change in frequency, amplitude and Q-factor as the Prothrombin reaction progressed. FIG. 9 shows an example of a Prothrombin reaction to a standard plasma (INR of 4.0).

Figure 10:
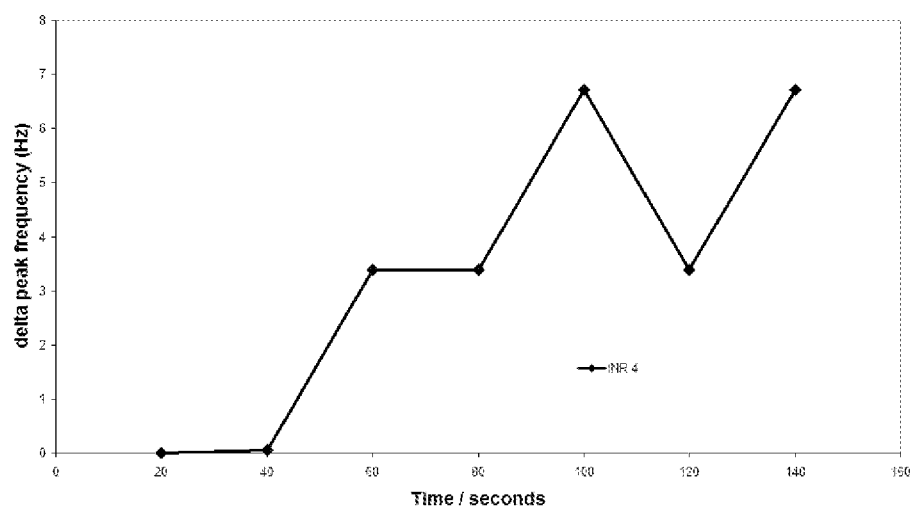
FIG. 10 shows a graph illustrating an example of the typical shift in peak frequency during a prothrombin reaction, this illustrating the relationship between INR and frequency.

From FIG. 10 it can be observed that during a typical prothrombin reaction the frequency only moves by approximately 7 Hz, whereas the Q-factor changes substantially. The density of the sample cannot change, as no matter is being added or taken away in this closed system. The viscosity of the sample changes significantly during the reaction.

Figure 11:
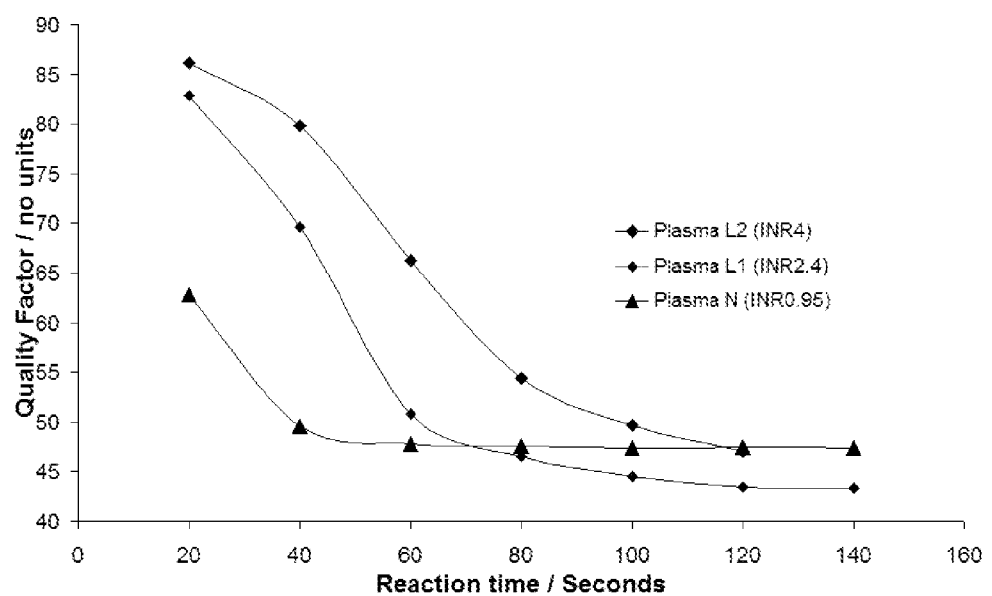
FIG. 11 shows a comparison of the Q-factor response of the sensor compared with time, for three different standards, wherein plasma standards with known INR values of 4.0 (large diamonds), 2.4 (small diamonds), and 0.95 (triangles) were tested for 140 seconds.

From the Q-factor results (as shown in FIG. 11) it was possible to clearly see the difference in the rates of the clotting reactions. The result of the "L2" standard plasma with an INR of 4.0 showed a much slower gelation reaction, compared with "L1" with an INR of 2.4 and the "N" standards with an INR of 0.95. From FIGS. 10 and 11 it can be observed that the viscosity of the liquid has a bigger effect on the Q-Factor compared to effect of viscosity on the frequency.

Figure 12:
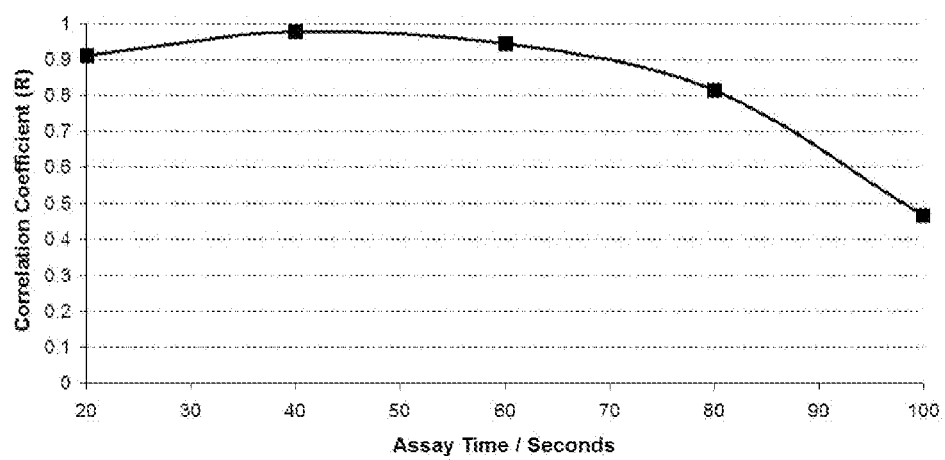
FIG. 12 shows a graph illustrating the relationship between the correlation coefficient and time, wherein an acceptable level of linearity is achieved provided a transient measurement is taken before 1 minute.

Further analysis of the data shown in FIG. 11 revealed that the correlation between INR and time varied throughout the experiment, as shown in FIG. 12. This data suggests that the optimum time to measure sensor output and to calculate the INR of sample is less than 60 seconds. A good correlation can be achieved in as little as 20 seconds.

Determination of the INR of Human Blood

Two healthy male donors who were not taking any anti-coagulation medication were sampled. The samples were treated in the same way as the plasma standards. Sensor results were obtained, an example of a prothrombin reaction in human blood is shown in FIG. 13.

Figure 13:
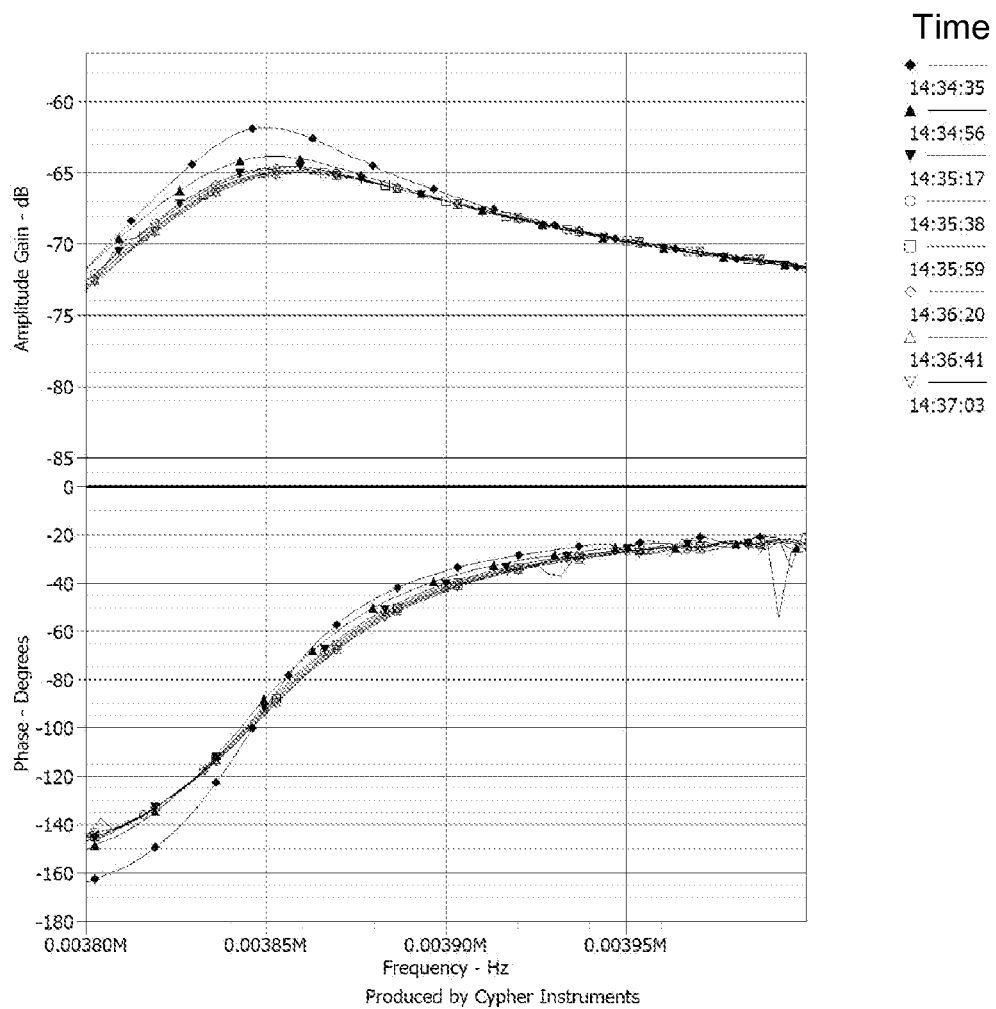
FIG. 13 shows a graph showing sensor responses to a Prothrombin reaction with a sample of whole human blood over 140 seconds, with three repeats being averaged for each sample.

Comparing the responses due to plasma samples as shown in FIG. 9, and the FIG. 13 the difference in the density of the two samples could be observed. In FIG. 13 the peak frequency of the first scan with the sensor in a whole blood sample when was first added to the sensor was approx. 3840 Hz, whereas the peak frequency of the first scan of the less dense plasma (as shown in FIG. 9) the peak frequency of the plasma solution was 3870 Hz.

Figure 14:
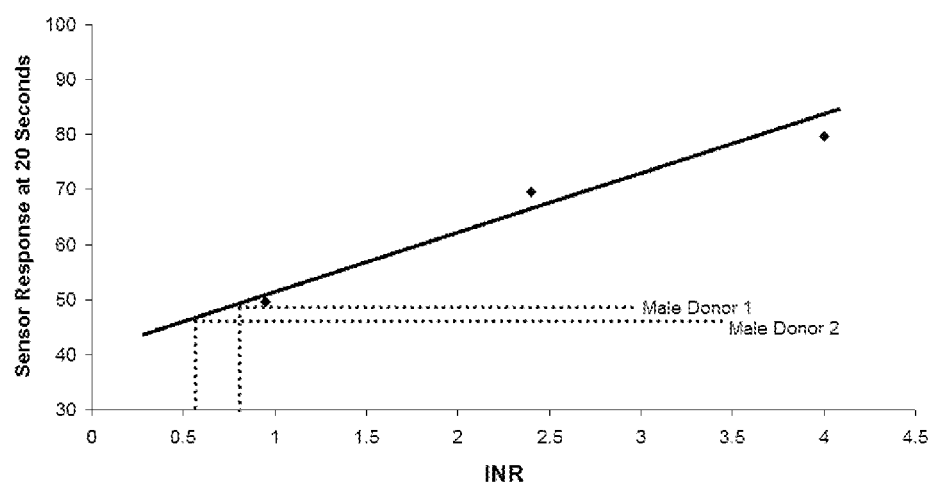
FIG. 14 shows a graph illustrating a determination of the INR of human blood using a triple beam resonating biosensor.

An evaluation of the relationship between the Q-factor and INR suggested that a linear fit can approximate the response in the range required. From the analysis as shown in FIG. 14 it can be observed that the two blood samples from the donors have INR values that concur with their health status. Donor 1 had an INR of 0.8, whilst Donor 2 had a measured INR of 0.6.

Example 2

Detection of Prothrombin Clotting Reaction with a Triple Beam Resonating Comprising Screen Printed Components This example demonstrates the concept of detecting the prothrombin clotting reaction with a triple beam resonator created using screen printed components.

Materials and Methods

The following materials were used for sensor fabrication:
Steel 200 pm from Precision Micro Ltd (Birmingham, UK)
Insulation 4924 (ESL, King of Prussia)
Gold Cermet Ink 8836 (ESL, King of Prussia)
PZT paste (D4 Technology, Southampton)
Silver Palladium Ink 9912-K (ELS, King of Prussia)
Protective Polymer 240-SB (ELS, King of Prussia) Double Side Tape 9975 (3M, Minneapolis, USA)
Hydrophilic Film 9971 (3M, Minneapolis, USA)
Medical Grade Polyester (Autotype, Oxon, UK)

The sensor fabrication process was as follows:

Triple beam resonating sensors were patterned in sheet steel using a standard photo-etching process. The triple beam resonator was configured with a centre beam that was 14 mm long, 2 mm wide and 0.2 mm thick, outer beams were 1 mm wide. The additional components required to drive the resonator were deposited using a thick film process. Insulation 4924 was deposited in such a way as to prevent the conductive tracks of the top and bottom electrodes from shorting. The base electrode for the PZT components was printed on top of the insulation using a gold compound 8836. A PZT paste was printed at the ends of the beams. A further gold electrode was printed over the top of the PZT to provide electrical connection. A silver-palladium track was created using compound 9912-K to connect the gold electrodes to the edge of the sensor where solder pads were created to allow connection to the remaining instrumentation. Stainless steel screens were used with a pitch of 320 threads per inch. The pastes were allowed to level, dried and fired as described in the manufacturer's specifications.

The devices were polled by applying in excess of 100V DC to the electrodes attached to the PZT, whilst the devices were heated to 200° C. After being removed from the carrier sheet, the tracks were insulated using a waterproof dielectric, 240-SB. The waterproof coat was cured at 200° C. for 2 hours.

The insulated sensors were fitted with a flow cell constructed from laminated construction tape. A layer of double sided tape such as 9975 was patterned to leave the beams unhindered and used to form a "spacer" layer between the base of the sensor and a sheet of polyester. A similar patterned piece double sided tape such as 9975 was placed on top of the sensor. A final piece of patterned polyester film was used to create a well.

For the convenience of performing this test, liquids were premixed and pipetted directly onto the sensor rather than filling the sensor by capillary action.

The instrumentation used was as follows:
Frequency Analyser (Cypher Instruments, London, UK)
Custom built amplifier (Cypher Instruments, London, UK)
Whirlimixer (Fisherbrand, UK)
Fibrinotherm and Custom Faraday Chamber (Highland Biosciences Ltd, Inverness, UK)
Assay Reagents Used
Manchester Capillary Prothrombin Time Test Kit—HB1133 FG (Hart Biologicals, Hartlepool, TS25 1TZ.)
Rabbit Brain Thromboplastin
Processed Sheep Plasma
Calibrated Reference Plasma
250407-N sample—INR Value 0.95
051206-L1 sample—INR Value 2.4
180506-L2 sample—INR value 4.0.
Reference Plasma The reference plasmas were prepared as per the manufacturer's instructions. Briefly, each sample was diluted using a physiological PBS buffer, and gently mixed to avoid frothing.

Procedure for INR Testing (i) Configuration of the Frequency Analyser

The frequency analyser was set to scan between 4610 and 4710 Hz, collecting 100 data-points. Each scan took ca. 6.5 seconds.

(ii) Analysis of the Plasma Standards and Donor Bloods

The three plasma standards (L1, L2 and N) and blood samples were analysed using the following protocol.

100 µl of reconstituted Manchester reagent was pipetted into an Eppendorf tube. The liquid was warmed to a temperature of 37° C., and left for at least 2 minutes. 20 pl of the plasma standard or blood sample was then added to the Manchester reagent. 35 pl of the mixture was then immediately pipetted onto the triple beam sensor. The faraday cage was closed and the frequency scan started.

Results and Discussion

Preparation of the INR Calibration Curve

Figure 15A:
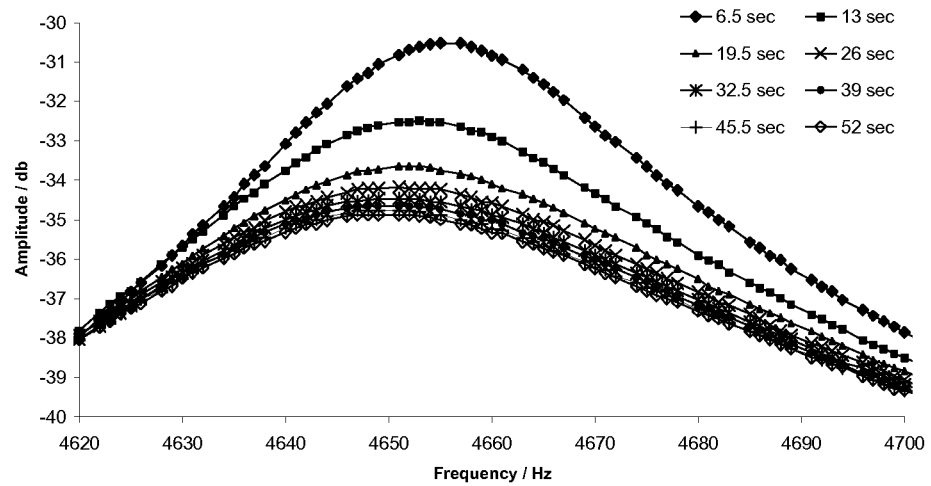
FIG. 15(A) and FIG. 15(B) show examples of the sensor response to a Prothrombin clotting reaction. A fast reaction due to a rapidly clotting sample having an INR value of 0.95 is shown (FIG. 15(A)), whilst a slowly clotting sample having an INR value of 4.00 is shown (FIG. 15(B))
Figure 15B:
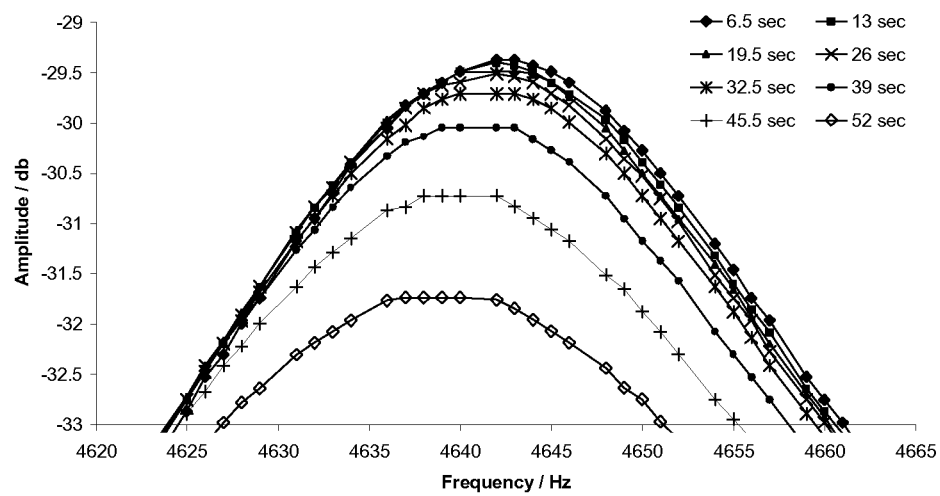

The frequency response plots were analysed to obtain the change in frequency, amplitude and Q-factor as the Prothrombin reaction progressed. FIG. 15(A) and FIG. 15(B) show examples of sensor responses.

FIG. 15(A) and FIG. 15(B) shows an example of the sensor response to a Prothrombin clotting reaction. A fast reaction due to a rapidly clotting sample having an INR value of 0.95 is shown in FIG. 15(A), whilst a slowly clotting sample having an INR value of 4.00 is shown FIG. 15(B).

FIG. 15(A) and FIG. 15(B) clearly shows that the sensor efficiently "tracks" the biochemical reaction. The faster clotting sample (INR 0.95) as shown in FIG. 15(A) shows the greatest rate of change in the frequency response within 26 seconds of the start of the reaction: the traces are spread far apart. The slower reacting sample (INR 4.0) as shown in FIG. 15 (A) shows a more gradual rate of change in the frequency response, hardly changing within the first 26 seconds of the start of the reaction. During the analysis same, the peak frequency of the analysis hardly changes at all.

Figure 16:
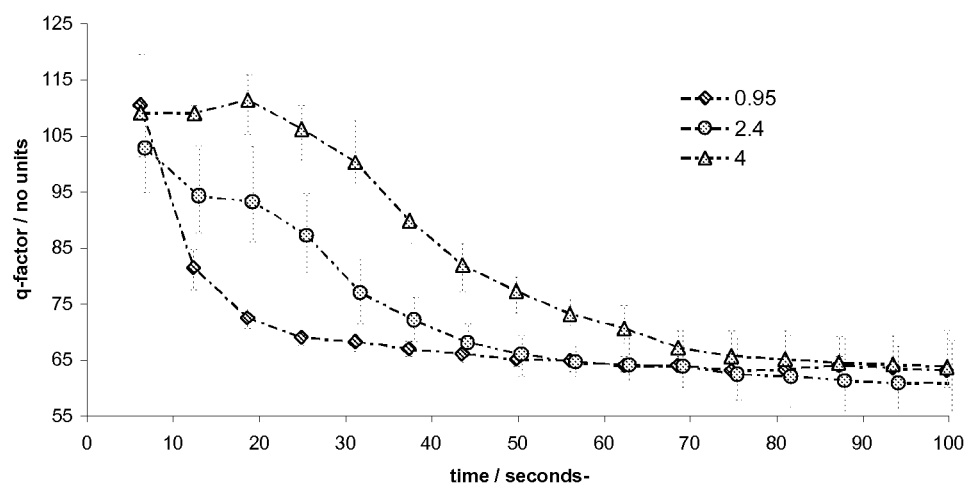
FIG. 16 shows a comparison of the Q-factor response of the sensor compared with time, for three different standards. Plasma standards with known INR values of 4.0 (triangles), 2.4 (circles) and 0.95 (diamonds) were tested for 140 seconds.

The reaction of each plasma standard was repeated four times and the average Q factor measurement was recorded with time, the results are plotted in FIG. 16.

FIG. 16 shows a comparison of the Q-factor response of the sensor compared with time, for three different standards. Plasma standards with known INR values of 4.0 (triangles), 2.4 (yellow triangles) and 0.95 (blue triangles) were tested for 140 seconds.

Figure 17:
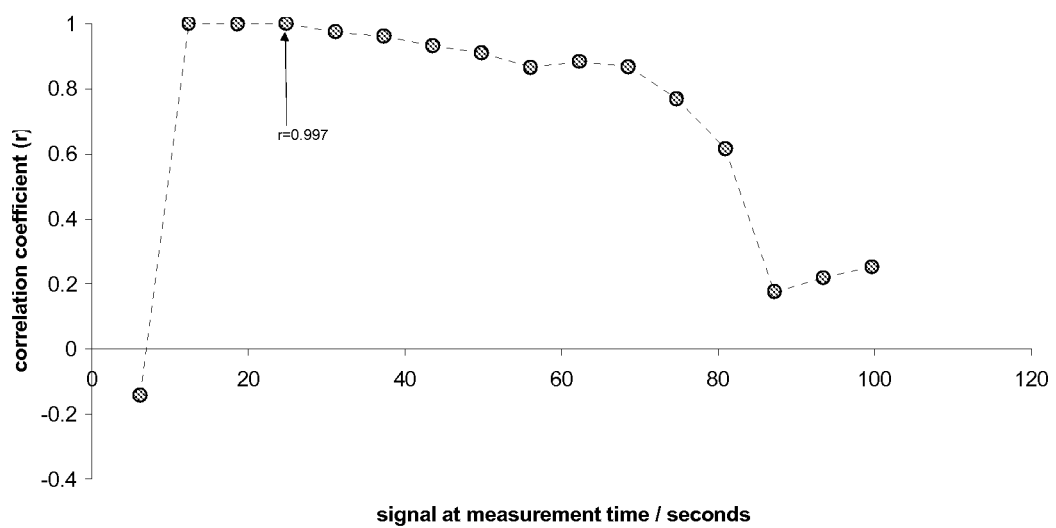
FIG. 17 shows a graph illustrating the correlation coefficient between responses and INR verses measurement time.

Further analysis of the data shown in FIG. 16 shows that the correlation between INR and time varied throughout the experiment, as shown in FIG. 17. This data suggests that optimum time to measure the sensor output and calculate the INR of sample is between 12 and 25 seconds. From the measurements made of the standard plasmas, it was possible to construct a calibration graph that related the known INR value against the Q-factor measured at 24 seconds.

Figure 18:
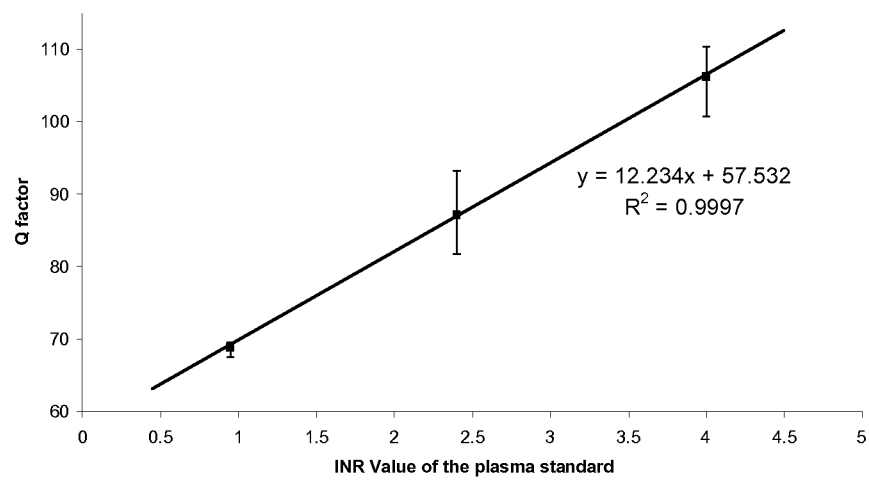
FIG. 18 shows that the correlation coefficient between INR and Q-factor obtained by an embodiment of the sensor which is produced by screen printing.

FIG. 18 shows that the correlation coefficient between INR and Q-factor. The correlation coefficient between the INR value and the Q-factor is linear, whilst the coefficient of variation of this sensor is better than 10%.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

What is claimed is:

1. A resonant sensor assembly for monitoring density and/or viscosity of a fluid comprising:
    a base substrate of fixed width and length;
    at least three parallel resonating beam members patterned in and integral to the base substrate, wherein the at least three beam members comprise a central beam member and at least two outer beam members, and wherein a width of the central beam member is twice the width of the at least two outer beam members such that a third mode of oscillation of the at least three beam members is optimally excitable;
    at least one vibration excitory element for use in providing a selective oscillation of at least one of the three beam members, wherein the at least one vibration excitory element is configured to cause at least one of the beam members to resonate in a transverse direction; and
    at least one sensor element for use in determining a frequency of oscillation of at least one of the at least three beam members, whereby density and/or viscosity of a fluid can be monitored by monitoring oscillations of at least one beam member.

2. The resonant sensor assembly according to claim 1, wherein the base substrate further comprising one or two side beams patterned in and integral to the base substrate parallel and spaced from the resonating beam members.

3. The resonant beam assembly according to claim 1, wherein the at least one vibratory excitory element and the at least one sensor element are positioned on the central beam at the ends of the resonant modes.

4. The resonant beam assembly according to claim 1, wherein the at least one vibration excitory element and/or the at least one sensor element comprise thick film screen printed PZT.

5. The resonant beam assembly according to claim 4, wherein the at least one vibration excitory element and the at least one sensor element are insulated by a waterproof coating.

6. The resonant beam assembly according to claim 1 further comprising conductive tracks for connecting the at least one vibratory excitation element and/or at least one sensor element to an external control unit, wherein the tracks are insulated by a waterproof coating.

7. The resonant beam assembly according to claim 5 further comprising conductive tracks for connecting the at least one vibratory excitation element and/or sensor element to an external control unit, wherein the tracks are insulated by a waterproof coating.

8. The resonant beam assembly according to claim 4, wherein the resonant beam members are stainless steel.

9. The resonant beam assembly according to claim 5, wherein the resonant beam members are stainless steel.

10. The resonant beam assembly according to claim 1, wherein the base substrate is rectangular.

11. The resonant beam assembly according to claim 10, wherein the at least 3 beam members are orthogonal to the length of the base substrate.

12. The resonant beam assembly according to claim 1, wherein data obtained in relation to at least one parameter derived from the resonance of at least one resonating beam is communicated to an analysis apparatus which is located remotely from the resonant beam assembly to monitor density and/or viscosity of the fluid.

13. A sensor device comprising:
    a resonant beam assembly including:
        a base substrate of fixed width and length;
        at least three parallel resonating beam members patterned in and integral to the base substrate, wherein the at least three beam members comprise a central beam member and at least two outer beam members, and wherein a width of the central beam member is twice the width of the at least two outer beam members such that a third mode of oscillation of the at least three beam members is optimally excitable;
        at least one vibration excitory element for use in providing a selective oscillation of at least one of the three beam members, wherein the at least one vibration excitory element is configured to cause at least one of the beam members to resonate in a transverse direction; and
        at least one sensor element for use in determining the frequency of oscillation of at least one of the at least three beam members, whereby density and/or viscosity of a fluid can be monitored by monitoring oscillations of at least one beam member; and
    a reaction chamber.

14. The sensor device according to claim 13, wherein the reaction chamber has a volume less than about 100 ml.

15. A method using a resonant beam assembly for monitoring density and/or viscosity of a fluid sample, the method comprising:
    using the resonant sensor assembly including:
        a base substrate of fixed width and length; and
        at least three parallel resonating beam members patterned in and integral to the base substrate, wherein the at least three beam members comprise a central beam member and at least two outer beam members, and wherein a width of the central beam member is twice the width of the at least two outer beam members such that a third mode of oscillation of the at least three beam members is optimally excitable;

providing a selective oscillation of at least one of three beam members via at least one vibration excitory element, wherein the at least one vibration excitory element is configured to cause at least one of the beam members to resonate in a transverse direction; and determining a frequency of oscillation of at least one of the at least three beam members via at least one sensor element, whereby density and/or viscosity of a fluid can be monitored by monitoring oscillations of at least one beam member.

16. A method for monitoring density and/or viscosity of a fluid sample before and/or during and/or after a chemical reaction, the method comprising:

providing a sensor device comprising:
a plurality of layers, wherein one of the layers comprises a base substrate layer, and
at least three parallel resonating beam members which are fixed to the base substrate layer at each end of their length at a fixed position, wherein the at the three beam members comprise a central beam member and at least two outer beam members, wherein a width of the central beam member is twice a width of the at least two outer beam members;

providing, by at least one vibration excitory element, a selective oscillation of at least one of the at least three beam members, whereby a third mode of oscillation of the at least three beam members is optimally excitable;

determining, by at least one sensor element, the frequency of oscillation of at least one of the at least three beam members; and receiving and retaining the fluid sample in a reaction chamber, wherein the reaction chamber accommodates the at least three beam members in a manner which allows the unimpeded oscillation of the at least three beam members whereby the density and/or viscosity of the fluid sample within the reaction chamber can be monitored by monitoring oscillations of at least one beam member within the reaction chamber.

* * * * *